United States Patent [19]
Carey et al.

[11] Patent Number: 5,827,478
[45] Date of Patent: *Oct. 27, 1998

[54] INCUBATION CHAMBER

[75] Inventors: Glen A. Carey, Grafton; Michael L. Malek, North Olmsted, both of Ohio

[73] Assignee: Chiron Diagnostics Corporation, East Walpole, Mass.

[*] Notice: The term of this patent shall not extend beyond the expiration date of Pat. No. 5,599,501.

[21] Appl. No.: 742,230

[22] Filed: Oct. 31, 1996

Related U.S. Application Data

[63] Continuation of Ser. No. 338,022, Nov. 10, 1994, Pat. No. 5,599,501.

[51] Int. Cl.⁶ .................................................. G01N 35/04
[52] U.S. Cl. .............................. 422/64; 422/63; 422/67; 436/43; 436/47; 436/49; 436/50; 436/54; 436/174; 436/175; 436/180
[58] Field of Search ................................ 422/63, 64, 67, 422/100, 104, 52; 436/43, 45, 47, 48, 49, 54, 174, 175, 179, 180, 164, 165, 172, 50

[56] References Cited

U.S. PATENT DOCUMENTS

| | | | |
|---|---|---|---|
| 3,623,381 | 11/1971 | Crepin | 74/822 |
| 3,740,143 | 6/1973 | Groner et al. | 356/39 |
| 3,741,875 | 6/1973 | Ansley et al. | 195/103.5 |
| 3,912,456 | 10/1975 | Young | 23/253 R |
| 4,058,367 | 11/1977 | Gilford | 23/253 R |
| 4,253,846 | 3/1981 | Smythe et al. | 23/230 R |
| 4,264,327 | 4/1981 | Blum | 23/230 B |

(List continued on next page.)

FOREIGN PATENT DOCUMENTS

| | | |
|---|---|---|
| 0226374 | 6/1987 | European Pat. Off. . |
| 0313008 | 4/1989 | European Pat. Off. . |
| 0336309 | 11/1989 | European Pat. Off. . |
| 0371265 | 6/1990 | European Pat. Off. . |
| 0397256 | 11/1990 | European Pat. Off. . |
| 0410645 | 1/1991 | European Pat. Off. . |
| 0411274 | 6/1991 | European Pat. Off. . |
| 0502638 | 9/1992 | European Pat. Off. . |
| 0601213 | 6/1994 | European Pat. Off. . |
| 2532763 | 8/1976 | Germany . |
| 3812978 | 7/1987 | Germany . |
| 3113372 | 5/1991 | Japan . |
| 3285172 | 12/1991 | Japan . |
| 4022867 | 1/1992 | Japan . |
| 6174728 | 6/1994 | Japan . |
| 1592299 | 7/1981 | United Kingdom . |
| 8000100 | 1/1980 | WIPO . |
| 8802866 | 4/1988 | WIPO . |
| 9222801 | 12/1992 | WIPO . |
| 9320450 | 10/1993 | WIPO . |

*Primary Examiner*—Long V. Le
*Attorney, Agent, or Firm*—Arthur S. Morgenstern; Charles L. Gagnebin, III; Robert P. Blackburn

[57] ABSTRACT

Method and apparatus for transportation and processing of multiple protocol assays within an automated immunoassay analyzer instrument. The apparatus includes a cuvette ring movably coupled to a magnet ring. In one embodiment, the magnet ring and cuvette ring are provided having circular shapes. A temperature controlled housing is disposed about the cuvette and magnet rings to provide a rotary incubation and particle separation chamber. The cuvette ring holds a plurality of cuvettes each of which may have a different assay disposed therein. The cuvette ring advances the cuvettes around the circumference of the incubation chamber. A plurality of discrete processing centers for aspiration and dispensing fluid samples, reagents and wash fluids are disposed at predetermined positions about the incubation chamber. The cuvette ring moves cuvettes in both clockwise and counter clockwise directions around the incubation chamber to position particular cuvettes at particular ones of the plurality of discrete processing centers to thus accommodate different protocols of each of the assays. By controlling the manner in which the cuvette ring moves within the incubation chamber, a plurality of different protocol assays each of which require different incubation times, can be simultaneously processed in the analyzer instrument.

20 Claims, 21 Drawing Sheets

U.S. PATENT DOCUMENTS

| | | | |
|---|---|---|---|
| 4,298,571 | 11/1981 | DiFulvio et al. | 422/65 |
| 4,303,611 | 12/1981 | Jessop | 422/65 |
| 4,487,700 | 12/1984 | Kanter | 210/789 |
| 4,528,159 | 7/1985 | Liston | 422/65 |
| 4,540,549 | 9/1985 | Manabe | 422/64 |
| 4,584,275 | 4/1986 | Okano et al. | 435/290 |
| 4,609,017 | 9/1986 | Coulter et al. | 141/1 |
| 4,629,703 | 12/1986 | Uffenheimer | 436/45 |
| 4,676,951 | 6/1987 | Armes et al. | 422/65 |
| 4,681,741 | 7/1987 | Hanaway | 422/100 |
| 4,708,940 | 11/1987 | Yoshida et al. | 436/45 |
| 4,731,225 | 3/1988 | Wakatake | 422/65 |
| 4,737,342 | 4/1988 | Herrmann et al. | 422/64 |
| 4,754,414 | 6/1988 | Gocho | 364/497 |
| 4,803,050 | 2/1989 | Mack | 422/65 |
| 4,818,493 | 4/1989 | Coville et al. | 422/102 |
| 4,857,272 | 8/1989 | Sugaya | 422/65 |
| 4,861,553 | 8/1989 | Mawhirt et al. | 422/65 |
| 4,906,433 | 3/1990 | Minekane | 422/64 |
| 4,925,629 | 5/1990 | Schramm | 422/82.05 |
| 4,927,769 | 5/1990 | Chang et al. | 436/518 |
| 4,928,540 | 5/1990 | Kido et al. | 73/864.11 |
| 4,931,402 | 6/1990 | Abplanalp | 435/291 |
| 4,971,913 | 11/1990 | Manabe et al. | 436/55 |
| 5,027,075 | 6/1991 | Harding, Jr. | 342/662 |
| 5,037,612 | 8/1991 | Takahashi et al. | 422/64 |
| 5,041,266 | 8/1991 | Fox | 422/102 |
| 5,051,238 | 9/1991 | Umetsu et al. | 422/64 |
| 5,089,424 | 2/1992 | Khalil et al. | 436/518 |
| 5,104,808 | 4/1992 | Laska et al. | 436/48 |
| 5,122,342 | 6/1992 | McCulloch et al. | 422/65 |
| 5,128,105 | 7/1992 | Berthold et al. | 422/104 |
| 5,147,529 | 9/1992 | Lee et al. | 210/695 |
| 5,171,532 | 12/1992 | Columbus et al. | 422/72 |
| 5,174,960 | 12/1992 | Shaw et al. | 422/63 |
| 5,178,834 | 1/1993 | Kagayama et al. | 422/65 |
| 5,196,168 | 3/1993 | Muszak et al. | 422/64 |
| 5,216,925 | 6/1993 | Odernheimer | 73/863.12 |
| 5,232,665 | 8/1993 | Burkovich et al. | 422/65 |
| 5,244,632 | 9/1993 | Shaw et al. | 422/63 |
| 5,244,633 | 9/1993 | Jakubowicz et al. | 422/64 |
| 5,270,007 | 12/1993 | Porte | 422/64 |
| 5,272,092 | 12/1993 | Hamasaki et al. | 436/172 |
| 5,286,651 | 2/1994 | Smith | 436/32 |
| 5,320,809 | 6/1994 | Dunn et al. | 422/64 |

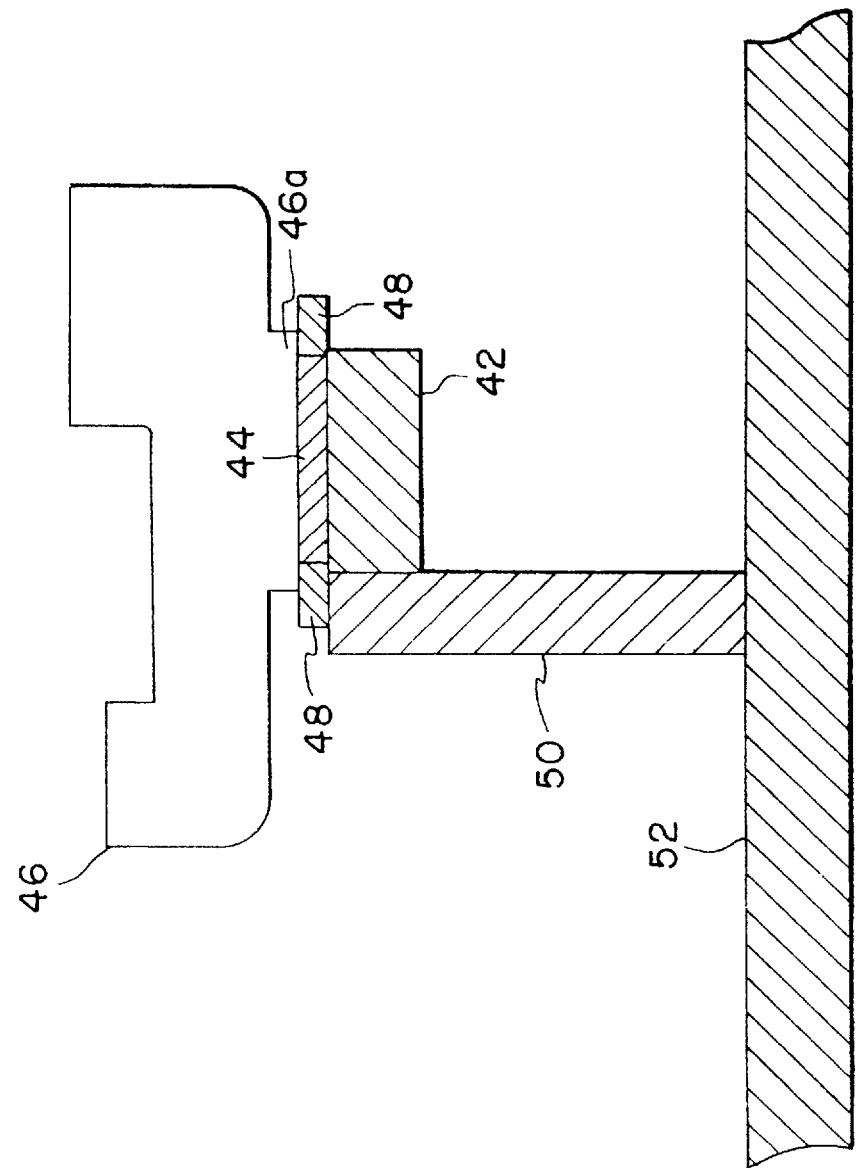

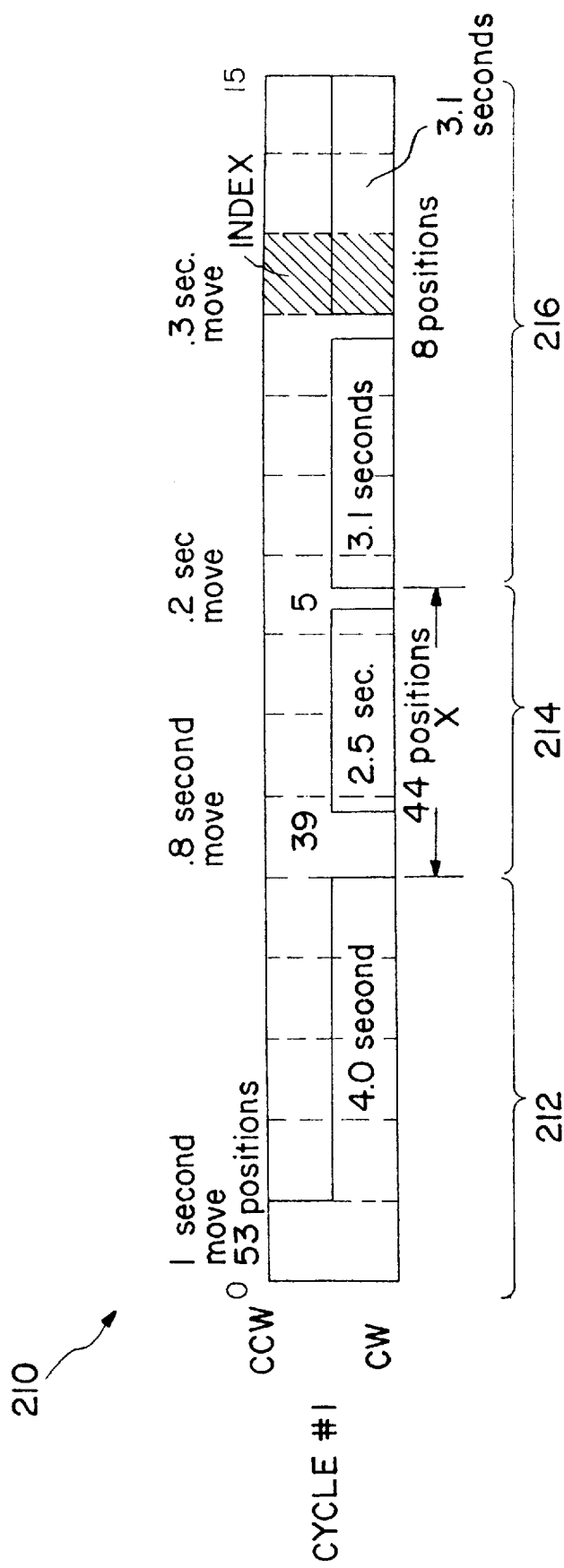

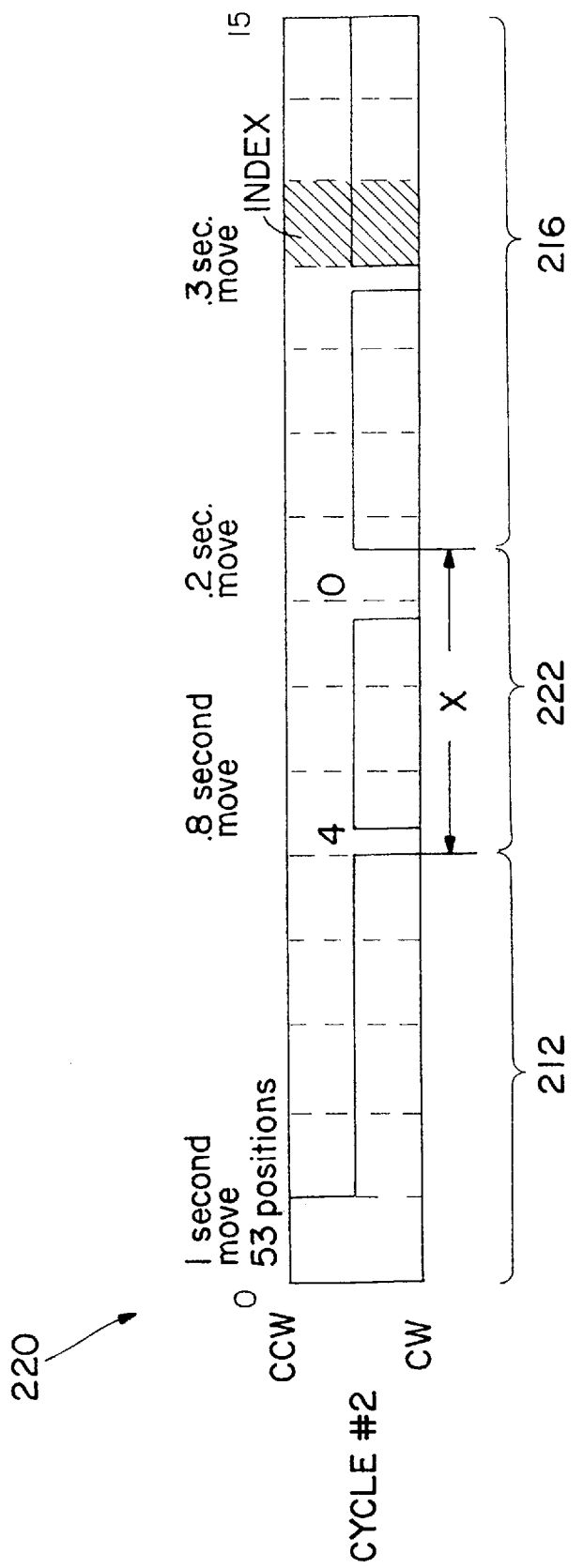

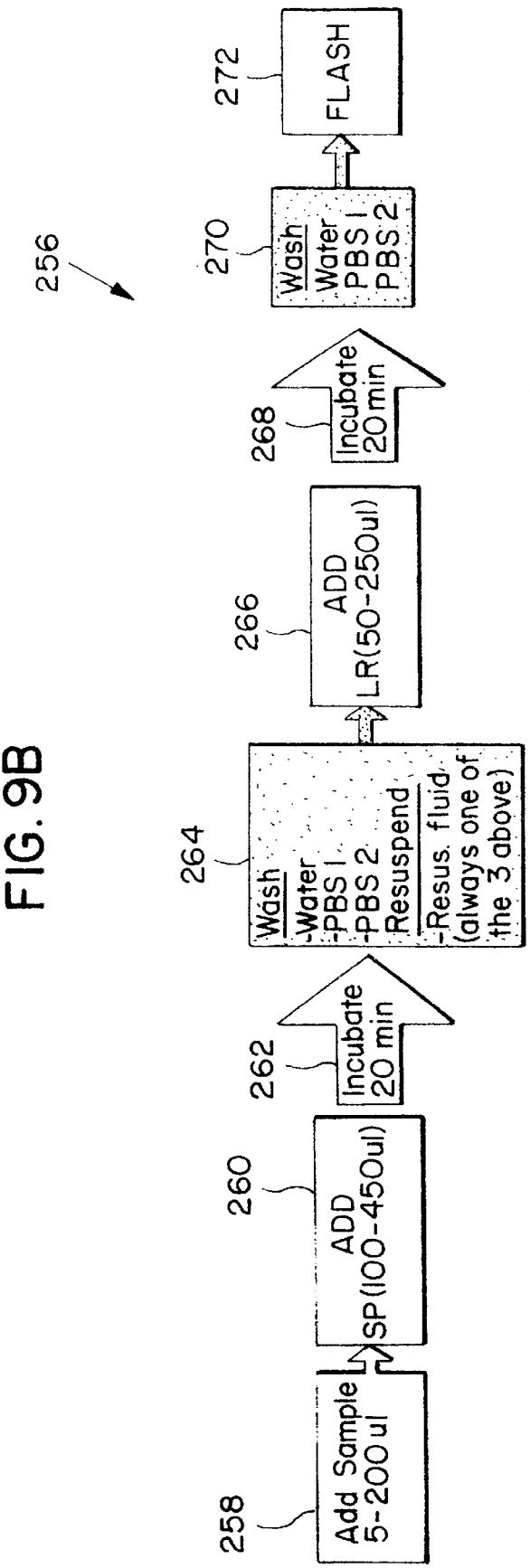

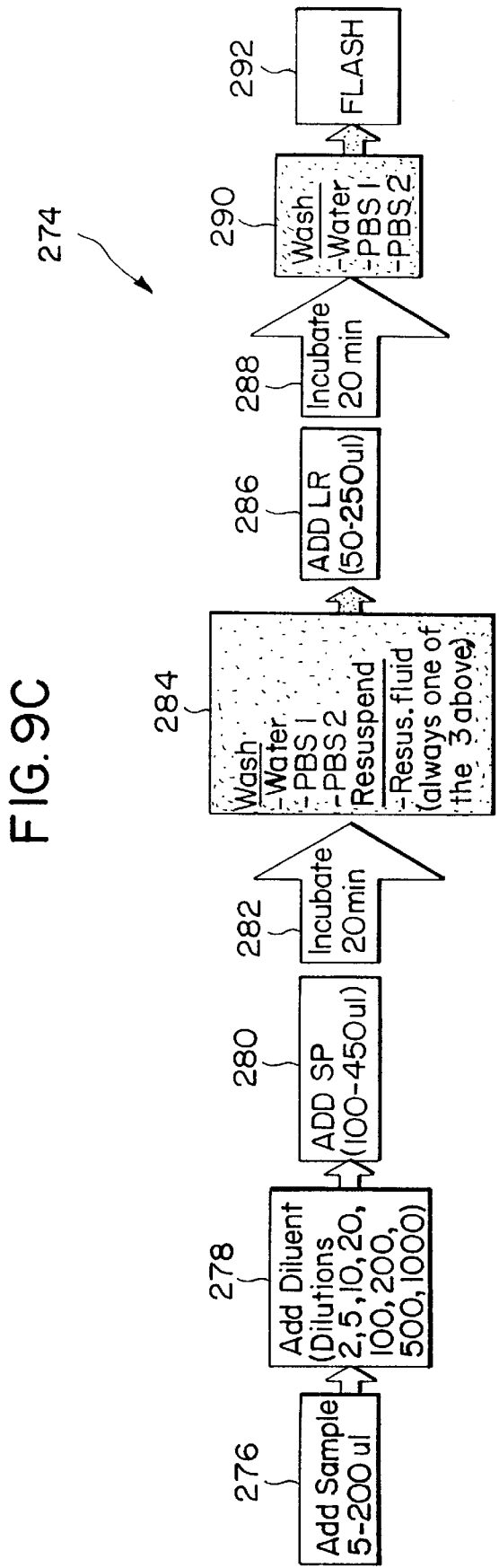

INCUBATION CHAMBER

This is a continuation of application Ser. No. 08/338,022 filed on Nov. 10, 1994, now U.S. Pat. No. 5,599,501.

FIELD OF THE INVENTION

This invention relates to automated immunoassay analyzer systems and more particularly to incubation chambers used in such systems.

BACKGROUND OF THE INVENTION

As is known in the art, there is a trend in hospitals, clinics, laboratories and other locations to perform tests (assays) on samples of patient specimens such as blood, spinal fluid, urine, serum, plasma, and the like using automated immunoassay analyzer systems. Relatively sophisticated automated analyzer systems typically accept a plurality of different patient specimen samples and perform different tests on each of the different samples. The samples may be diluted or otherwise treated depending upon the type of analyzer system used, the type of assay being performed, and other factors including but not limited to the desired analyte concentration.

The samples are typically placed in a container such as a sample cup or a primary tube for example, which is then placed in the analyzer system. One or more appropriate chemical reagents needed to perform the assays are also placed in the analyzer system. The reagents are typically mixed with the samples in the analyzer system via a fluid moving system generally provided as a pipette controlled by a robotic arm. The pipette is adapted to aspirate portions of the reagents and/or samples and dispense them into appropriate ones of the cuvettes where a reaction can take place.

Different types of assays may require different amounts of the sample specimen, different amounts of reagents, different processing steps, different incubation times, etc . . . Thus one problem which arises in automated analyzer systems is that it may be necessary to reset the system and load different reagents or it may even be necessary to re-program the automated analyzer system prior to processing a new assay.

For example, even if only a few of several different types of assays need to be run, the operator-user must load and run the analyzer system for the first type of assay and then after the testing on the first type of assay is complete, the operator-user must reload and reset the analyzer system to run the next different type of assay on another batch of samples using perhaps different reagents and so on. These steps are repeated until all of the different assays are complete. Thus, although such automated analyzer systems can provide assay results more quickly and conveniently than manual approaches, overall throughput of the analyzer system is not maximized.

It would be desirable therefore to provide an automated analyzer system capable of processing more than one type of assay on specimen samples in an unattended run and capable of performing different types of assays on a number of different specimen samples simultaneously without resetting the analyzer system or reloading reagents or other chemicals in the analyzer system prior to processing the different types of assays to thus increase the overall throughput of the analyzer system.

SUMMARY OF THE INVENTION

In accordance with the present invention, an automated immunoassay analyzer instrument includes a continuous closed loop incubation chamber and a plurality of processing centers disposed about the incubation chamber with each of the plurality of processing centers for aspiration and dispensing of at least one of specimen samples, reagents, and wash fluids. The incubation chamber includes a continuous closed loop cuvette track for moving cuvettes in first and second opposite directions around the incubation chamber such that particular ones of plural cuvette slot positions in the cuvette track are positioned proximate particular ones of the plurality of processing centers at predetermined periods of time during a predefined cycle time. With this particular arrangement, an automated random access immunoassay analyzer instrument capable of performing a plurality of different assays each of such assays having different protocols is provided. By providing the incubation chamber as a continuous loop, different incubation times may be accommodated by allowing an assay in a cuvette to complete multiple revolutions around the incubation chamber. Additionally, since the cuvette track can move cuvettes in any direction around the incubation chamber, the motion sequence of the cuvette track can be adjusted to accommodate different assay requirements. For example, specimen samples and reagents may be added to cuvettes at times selected to adjust the incubation time of the cuvette. The automated immunoassay analyzer instrument further includes a continuous closed loop magnet track to which the cuvette track is movably coupled to thus provide the incubation chamber as an incubation and particle separation chamber in which paramagnetic particle separation may be performed in each of the cuvettes. In preferred embodiments, the cuvette track and magnet track are each provided having circular or ring shapes to thus provide the incubation and particle separation chamber as a rotary incubation and particle separation chamber. The assays may be processed by a scheduler in the analyzer instrument on a first-in-first-out (FIFO) basis or alternatively the process scheduler may be used to determine a particular order in which particular tests should be performed to thus maximize throughput of the analyzer system. In this manner the system is capable of processing a large number of assays in a predetermined period of time. For example, in one embodiment, the system can process about two-hundred and forty assays per hour.

In accordance with a further aspect of the present invention, an automated immunoassay analyzer instrument includes a magnet ring having a magnet assembly coupled thereto, a cuvette ring movably coupled to the magnet ring and a drive system coupled to the magnet ring for moving the magnet ring in first and second opposite directions. With this particular arrangement an automated immunoassay analyzer instrument for performing multiple protocol assays including paramagnetic particle separation assays is provided. By moving the cuvette ring relative to the magnet ring, cuvettes containing assays are moved past the magnet assembly. Paramagnetic particles in the cuvette are attracted to one region of the cuvette by a magnetic force provided from the magnet assembly to thus perform paramagnetic particle separation. In one embodiment, the drive system includes a servo motor coupled to the magnet ring by a belt. The servo motor turns the belt to drive the magnet ring at high speeds. By providing the belt as a steel belt which does not tend to stretch, the servo motor may precisely position each of the cuvettes in the cuvette ring at predetermined points around the incubation chamber. The steel drive belt can be pinned to the magnet ring to thus minimize slippage between the drive belt and magnet ring and thus allow the magnet ring to be driven at high speeds while still maintaining the ability to accurately position the magnet ring at predetermined locations around the incubation chamber. In an alternate embodiment, the steel belt can be coupled to the magnet ring via friction. The cuvette ring can be coupled to the magnet ring via a detent pin which locks the cuvette ring to the magnet ring. The analyzer instrument further includes an index mechanism for disengaging the detent pin to thus allow the cuvette ring to move relative the magnet ring. Upon completion of a movement of the cuvette ring relative the magnet ring, the detent pin re-engages the detent pin to re-lock the cuvette ring to the magnet ring. In this manner each cuvette in the cuvette ring can be advanced past the magnet assembly coupled to the magnet ring to thus facilitate paramagnetic particle separation in each of the cuvettes. The magnet assembly may be provided from one or more magnets. In a preferred embodiment, the magnet assembly includes two pairs of magnets spaced by a predetermined distance. With this arrangement a particle re-suspend operation can be performed in a cuvette which is positioned in the space between the two pairs of magnets.

BRIEF DESCRIPTION OF THE DRAWINGS

The foregoing features of this invention as well as the invention itself may be more fully understood from the following detailed description of the drawings in which

FIG. 1B is a cross sectional view of a portion of an automated immunoassay analyzer system taking along lines 1B—1B of FIG. 1A;

FIGS. 8–8B are a series of diagrams illustrating cycle timings in an incubation chamber;

DESCRIPTION OF THE PREFERRED EMBODIMENTS

Figure 1:
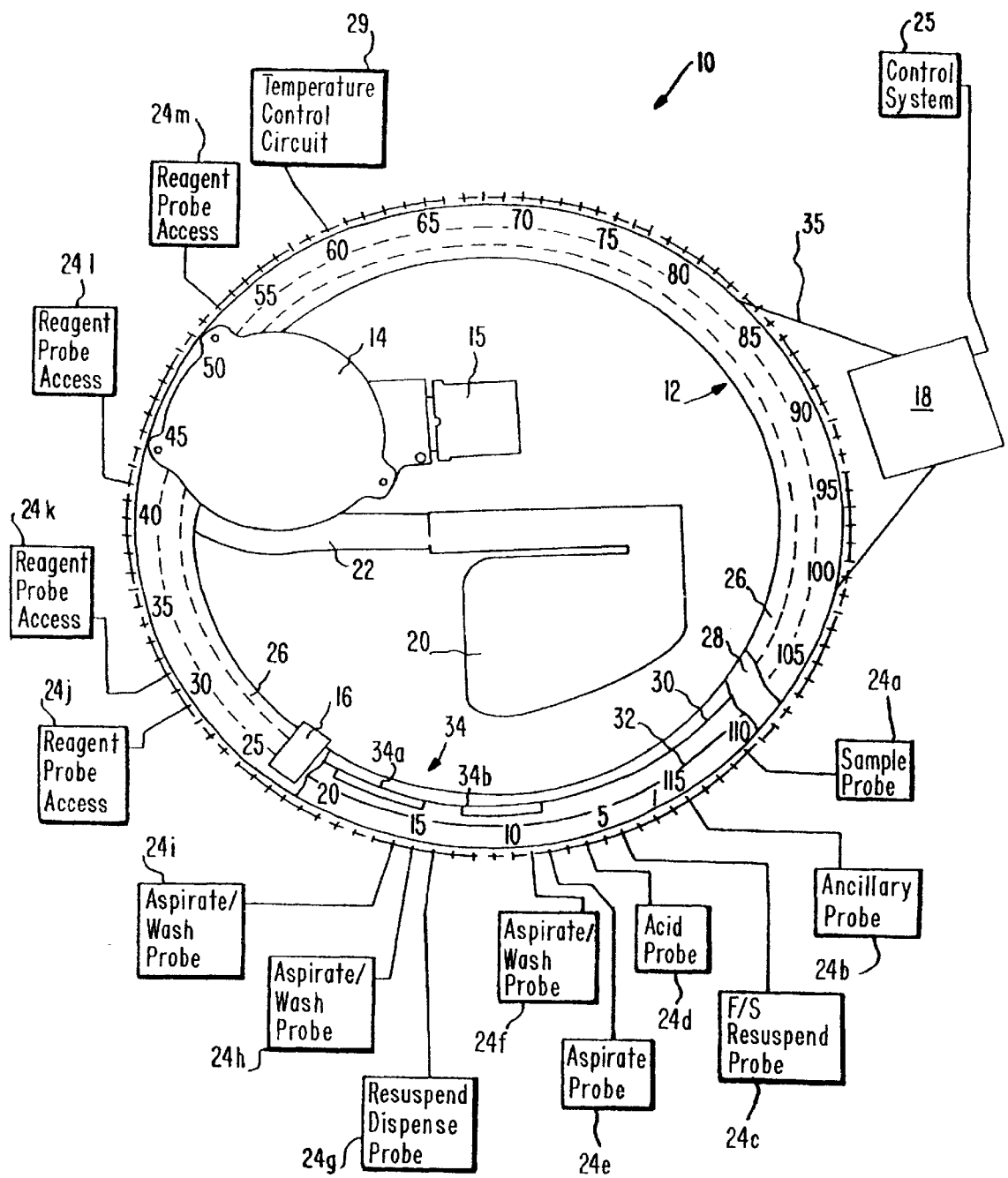
FIG. 1 is a diagrammatical top view of an automated immunoassay analyzer system.

Referring now to FIG. 1, an automated immunoassay analyzer instrument 10 includes an incubation chamber 12 having coupled thereto a luminometer 14 and photomultiplier tube 15, an index mechanism 16, a drive assembly 18, a cuvette feeder 20, a preheat chamber 22 and a plurality of probe stations 24a–24m generally denoted 24. A microprocessor based control system 25 is coupled to and controls the operation of the automated analyzer instrument 10.

The analyzer instrument processes assays which are contained within the analyzer instrument in separate containers referred to as cuvettes. The microprocessor based control system 25 includes a scheduler which determines a particular order in which to process assays. For example, the assays may be performed on a first-in-first-out (FIFO) basis. Alternatively, the scheduler may determine a particular order in which assays should be performed by using a Greedy algorithm, for example, to thus maximize throughput of the analyzer instrument 10. The analyzer instrument 10 is thus provided as a random access immunoassay analyzer instrument capable of processing a plurality of different protocols and assays.

The incubation chamber 12 is provided from an insulative housing 26 portions of which have here been removed to reveal a chamber housing 28 over which the insulative housing 26 is disposed. As will be described further below in conjunction with FIGS. 2–4, the chamber housing 28 includes temperature control means 40 FIG. (1A) to which is coupled a temperature control circuit 29 which sends control signals to the temperature control means 40 to thus control the temperature of the chamber housing 28.

Portions of the temperature controlled chamber housing 28 have here been removed to reveal that the incubation chamber 12 also includes a magnet ring 30 and a cuvette ring 32 over which the chamber housing 28 is disposed.

The cuvette ring 32 is provided having a plurality of slots formed therein each of such slots adapted to accept a cuvette. In this particular embodiment the cuvette ring 32 has 115 cuvette slots and can thus hold 115 cuvettes each of which may have an assay disposed therein. Those of ordinary skill in the art will appreciate of course that the system 10 could alternatively be provided having cuvette and magnet rings sized such that the cuvette ring has greater or fewer than 115 cuvette slots.

In FIG. 1 each of the 115 cuvette slots in the cuvette ring 32 have been labeled with a numerical reference designation from 1 to 115. It should be noted that the numerical reference designation of the cuvette slots have been arbitrary assigned and are included here only to assist in explaining and understanding the operation of the incubation chamber 12.

As will be described in detail below in conjunction with FIGS. 2 and 6, the cuvette ring 32 is movably coupled to the magnet ring 30 such that the cuvette ring 32 can move relative to the magnet ring 30.

The magnet ring 30 has a magnet assembly 34 coupled thereto. The magnet assembly 34 in this particular embodiment includes a pair of magnets 34a, 34b spaced by a predetermined distance here corresponding to a single cuvette slot.

The cuvette feeder 20 and preheat chamber 22 will be described in detail in conjunction with FIG. 3 below. Suffice it here to say, however, that cuvettes placed into the cuvette feeder 20 are fed into the preheat chamber 22 which leads to a cuvette entrance chute of the incubation chamber 12. Cuvettes are fed through the cuvette entrance chute and are disposed into the slots of the cuvette ring 32. The cuvette ring 32 thus holds the cuvettes as the cuvettes move around the incubation chamber 12.

The assays in each of the cuvettes may have different protocols. That is the assays may have different incubation times, different reagent addition times, different wash cycles, etc. For example, a single pass assay cycle generally describes an assay having an incubation time period typically of about eight minutes and which passes by the magnets 34 and wash stations 24f, 24h, 24i only once. The incubation time corresponds to the time between when a reagent is added to a cuvette until the time the cuvette reaches a first one of the magnets 34a, 34b in the magnet assembly 34. Thus, as will be described in detail in conjunction with FIG. 9 below, an eight minute incubation time is achieved by adding a reagent to a cuvette which is positioned in the cuvette ring 32 such that the cuvette will not reach the magnet assembly 34 for about eight minutes.

Other assays, however, may require longer incubation times. For example some assays may require an incubation period typical of about eighteen minutes. Thus, as will also be described in conjunction with FIG. 9 below, to achieve an eighteen minute incubation period, a reagent is added to a cuvette positioned in the cuvette ring 32 which will not reach the magnet assembly 34 for a time period of about eighteen minutes.

It should also be noted that since the incubation chamber 12 is provided as a continuous loop, cuvettes may make multiple revolutions around the incubation chamber 12 and thus pass by the magnets 34a, 34b and wash stations 24f, 24h, 24i two or more times.

Thus, providing the incubation chamber 12 as a continuous track or loop avoids the necessity of having a plurality of different magnet assemblies, probe stations and wash stations thus reducing the need for extra parts and thereby reducing cost and increasing the reliability of the analyzer system 10. That is, by providing the incubation chamber 12 as a continuous track, cuvettes can be moved past processing stations multiple times thereby minimizing the number of protocol specific components included in the analyzer system 10.

It should be noted that although the incubation chamber 12 is here shown having a circular or ring shape, in other embodiments it may be desirable for the incubation chamber 12 to be provided having a rectangular shape, a triangular shape, an oval shape or any other shape which allows the incubation chamber 12 to be provided as a continuous track. The particular shape of the incubation chamber 12 may be selected in accordance with a variety of factors including but not limited to size, cost and space requirements of the incubation chamber 12 and analyzer system 10.

In operation, cuvettes are placed in the hopper feeder 20 and are fed down a chute to the preheat chamber 22 where the cuvettes are heated to a temperature typically of about 37 degrees centigrade (° C). The preheat chamber 22 is coupled to the temperature control circuit 29 which controls the temperature of the preheat chamber 22 independently of the temperature of the incubation chamber 12. Thus, the preheat chamber 22 can be heated or cooled to any temperature independent of the temperature of the incubation chamber 12.

As will be described in conjunction with FIG. 3 below, the cuvettes are then moved through the preheat chamber 22 and fall through a cuvette entrance chute into one of the plurality of cuvette slots in the cuvette ring 32.

The drive assembly 18 is coupled to the magnet ring 30 of the incubation chamber 12 via a metal belt 35 having openings formed therein to accept corresponding studs or teeth projecting from an outer first surface of a drive pulley coupled to the drive assembly 18. By providing the incubation chamber 12 having a circular shape, the drive assembly 18 can be provided as a bi-directional servo motor having the metal belt 35 coupled between the magnet ring 30 and the drive pulley of the bi-directional motor 18. It should be noted that the servo motor could alternatively be provided as a stepper motor and the belt could be provided from a non-stretch material which is not metal. For example, in some embodiments it may be desirable to provide the belt 35 as a polyurethane belt having one or more stainless steel cables disposed therein.

In a preferred embodiment, the belt 35 is provided from steel to thus minimize belt stretching which would result in less accurate positioning of the magnet ring 30, and thus cuvettes, with respect to the probe stations 24. To further increase the accuracy with which the drive system 18 can position cuvettes and as will be described below in conjunction with FIG. 4, a first end of the belt 35 can be fixed to the magnet ring 30.

In alternate embodiments, however, a friction coupling may be provided between the belt 35 and the magnet ring 30. Alternatively still, in some applications it may be desirable to drive the cuvette or magnet ring using gears rather than a belt. In yet other applications, the cuvette or magnet ring may be driven by a chain coupled between one of the rings and the motor 18. Suffice it to say that there are a plurality of means which can be used to couple the motor 18 to the rings 30, 32.

The plurality of probe stations 24 are disposed around the circumference of the incubation 12 at predetermined locations and are arranged to aspirate and/or dispense fluids from/to cuvettes at fixed positions around the circumference of the incubation chamber 12. Thus, the cuvette ring 32 must rotate the cuvettes around the circumference of the incubation chamber 12 to position cuvettes at particular cuvette positions such that particular probe stations 24 can access the cuvettes to thereby allow particular operations to be accomplished at predetermined periods of time. A sample probe 24a is aligned at position 111 of the cuvette ring 32. Fluid samples which have been aspirated by the sample probe are dispensed into which ever cuvette is aligned with position number 111 of the cuvette ring 32. Therefore, in order to dispense a sample into a particular cuvette, the cuvette must be aligned under position number 111 of the cuvette ring 32. Similarly, an ancillary probe 24b is aligned to dispense ancillary reagents into a cuvette which is aligned at position 115 of cuvette ring 32. Thus, a cuvette which requires an ancillary reagent must be aligned at position 115 of the cuvette ring 32. Likewise, a re-suspend probe 24c is aligned with position 4 of the cuvette ring 32 and thus a cuvette which requires a re-suspend fluid must be aligned at position 6 of the cuvette ring 32. Likewise, an acid probe 24d is aligned to dispense acid into a cuvette which is aligned with position 6 of the cuvette ring 32 and thus a cuvette which requires an acid dispense must be aligned at position 6 of the cuvette ring 32. Likewise, an aspirate probe 24e is arranged to aspirate fluid from a cuvette which is aligned with position 8 of the cuvette ring 32. A aspirate/wash probe station 24f is aligned to access cuvettes at position 9 of the cuvette ring 32. A re-suspend dispense probe 24g is arranged to dispense a fluid into a cuvette positioned between the magnets 34a, 34b at position number 9 of the cuvette ring 32 to thus re-suspend particles in the cuvette. A pair of wash and aspirate probes 24h, 24i are arranged to process cuvettes which aligned with positions 15 and 16 respectively of the cuvette ring 32.

A plurality of reagent probe access stations 24j–24m are aligned to dispense reagents into cuvettes which are respectively aligned with positions 29, 31, 42, and 53 of the cuvette ring 32. The insulative and chamber housings 26, 28 are provided having holes or spaces therein to allow the probes to access the cuvettes through the housings 26, 28. It should be noted that some of the probes 24i–24l may use the same holes in the housings 26, 28. However, such use cannot be simultaneous. It should also be noted that it may be possible in some embodiments to have a single probe perform more than one function. For example, a single probe may dispense reagents at either position 29 or position 31 of the cuvette ring 32.

Depending on the type of assay being performed, particular ones of the reagent, aspirate/wash probes, dispense probes and acid probes are used. It should be noted that every probe is not used during the processing of every assay. Rather only particular probes are used during the processing of particular assays.

As shown in FIG. 1, the magnet index assembly 16 is aligned at position 23 of the cuvette ring 32. As will be described in detail in conjunction with FIG. 6 below, magnet index assembly 16 allows the cuvette ring 32 to move relative the magnet ring 30 and thus the magnets 34a, 34b.

It should also be noted that although the magnets 34a, 34b are here spaced by a single cuvette slot, in other embodiments it may be desirable to space the magnets 34a, 34b by a plurality of positions or alternatively to juxtapose the magnets 34a, 34b such that there is no gap between the magnets 34a, 34b. The spacing between the magnets 34a, 34b may thus be selected in accordance with a variety of factors including but not limited to the particular type of assays being performed in the analyzer system 10.

Figure 1A:
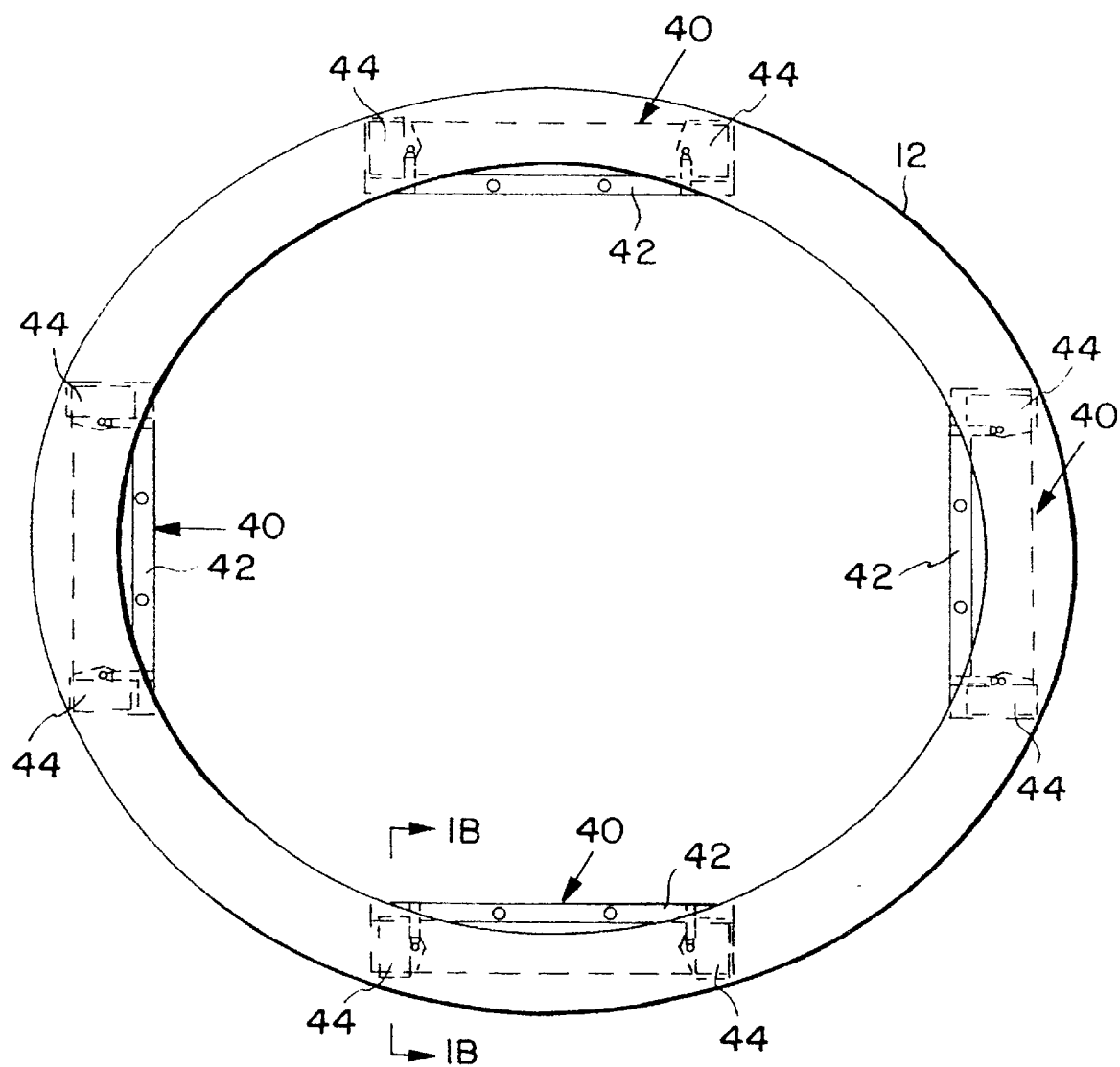
FIG. 1A is a diagrammatical top view of a portion of an automated immunoassay analyzer system.

Referring now to FIG. 1A, a plurality of temperature control means 40 are coupled to the incubation chamber 12 to maintain the incubation chamber 12 at a predetermined temperature. In this particular embodiment, four temperature control means 40 are coupled to the incubation chamber 12. It should be noted, however, that fewer or more than four temperature control means 40 can be used.

The precise number of temperature control means 40 should be selected such that the temperature of the incubation chamber 12 can be regulated and evenly maintained at a predetermined temperature. It should also be noted that each of the individual temperature control means 40 are coupled to the temperature control circuit 29 and that in some applications, it may be advantageous to set each of the means 40 at a different temperature.

In this particular embodiment, each of the temperature control means 40 includes a mounting member 42 having a thermal electric device 44 (TED) mounted on opposite ends thereof. The particular manner in which the TEDs 44 are mounted to the member 42 and coupled to the incubation chamber 12 will be described below in conjunction with FIG. 1B. Suffice it here to say that the TEDs 44 are coupled to the incubation chamber 12 and can either heat or cool the incubation chamber 12 to thus maintain the temperature of the incubation chamber 12 within a predetermined range of temperatures. Thus, in this particular embodiment, the temperature control means 40 is provided from eight TEDs 44 mounted in pairs on four TED mounting blocks 42 each of which are coupled to the mounting plate 52 by thermally conductive support member 50.

Referring now to FIG. 1B, in which like elements of the heating means 40 of FIG. 1A are provided having like reference designations, the base ring 46 of the incubation chamber 12 (FIG. 1A) includes a step region 46a on which a thermal electric device (TED) 44 is disposed. An insulating member 48 is disposed about the TED 44 to position the TED 44 with respect to the base ring step 46a and to thermally isolate the base ring 46 from the TED mounting member 42 and a support member 50. The TED mounting member 42 and the support member 50 are each provided from a thermally conductive material such as aluminum, for example to thus provide a thermally conductive path between the TED 44 and a mounting plate 52.

The insulating member 48 is provided having an aperture therein with the shape of the aperture selected to substantially match the shape of the TED 44. For example, if the TED 44 is provided having a rectangular shape, then the insulating member 48 is provided having a rectangular shaped aperture provided therein. Thus, a first surface of the TED 44 contacts a bottom surface of the base ring 46 and a second surface of the TED 44 contacts the mounting member 50. The TED 44 is thereby coupled to the thermal path provided by the mounting member 50 and support member 50.

The mounting plate 52 supports the incubation chamber 12. In preferred embodiments, the mounting plate 52 is also provided from a thermally conductive material to thus absorb any thermal energy transmitted from the TEDs 44 through the TED mounting block 42 and through the thermally conductive support member 50.

Figure 2:
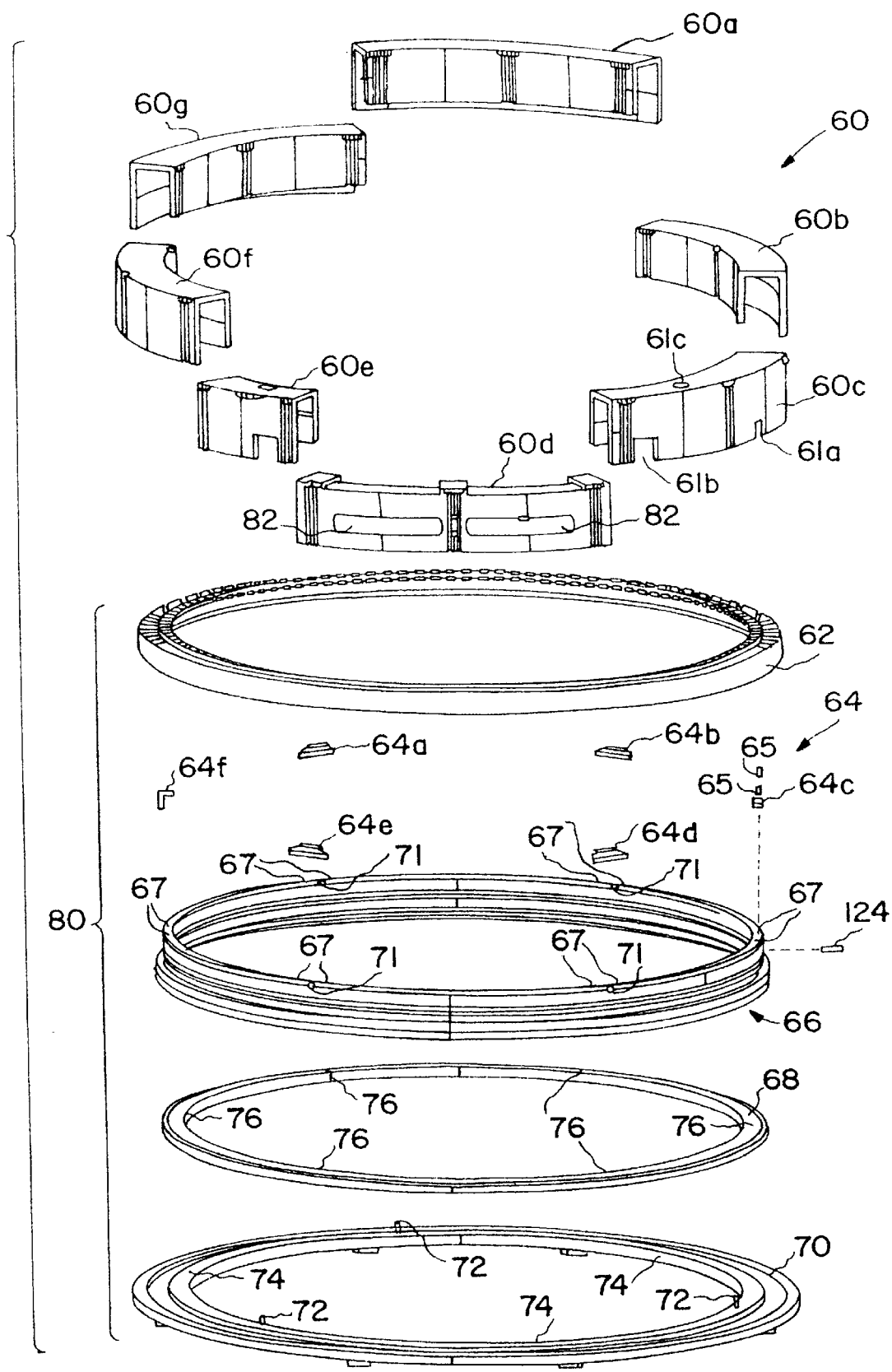
FIG. 2 is an exploded view of an incubation chamber.

Referring now to FIG. 2, the incubation chamber 12 includes a cover 60 here provided from a plurality of sub-cover sections 60a –60g which are disposed over a cuvette ring 62. The incubation chamber 12 further includes a plurality of cuvette ring bearings 64a–64f generally denoted 64, a magnet ring 66, a magnet ring bearing 68 and a base ring 70.

The cuvette ring 62 is provided as a circular aluminum ring having 115 slots provided therein with each of the slots sized to accommodate a cuvette. The cuvette ring 62 is movably coupled to the magnet ring 66 via the cuvette ring bearings 64a–64f.

In this particular embodiment, each of the cuvette ring bearings 64 are provided having a substantially L shaped cross section. The bearings 64 can be provided from plastic or any other material well known to those of ordinary skill in the art having sufficient strength to support the cuvette ring 62 while also allowing the cuvette ring 62 to rotate freely with respect to the magnet ring 66.

A first or bottom surface of each of the cuvette ring bearings 64 are disposed on a top surface of the magnet ring 66. The cuvette ring 62 is disposed over the cuvette ring bearings 64 and a bottom surface of the cuvette ring 62 contacts a second or top surface of each of the cuvette ring bearings 64. Thus, the cuvette ring bearings 64 act as friction type bearings which provide a region on which the cuvette ring 62 seats.

In this embodiment, the cuvette ring 62 and magnet ring 66 are provided having an inside diameter typically of about 20 inches. It is thus relatively difficult to maintain tight tolerances during fabrication of the cuvette and magnet rings 62, 66. The cuvette ring bearings 64 therefore are preferably positioned about the magnet ring 66 to accommodate for the inaccuracies, machining tolerances and other imperfections resultant from fabricating the cuvette and magnet rings 62, 66 to thus ensure that the cuvette ring 62 properly seats on the magnet ring 66. Also, and as will be described below, the cuvette ring bearings 64 insure the cuvette ring 62 moves freely relative the magnet ring 66.

Each of the cuvette ring bearings 64 are coupled to the magnet ring 66 via a pair of screws 65 and a set screw 124 which mate with threaded holes 67 and 71 respectively in the magnet ring 66. Here, only a single pair of screws 65 and a single set screw 124 are shown. The set screws 65 can be tightened to secure the cuvette ring bearings 64 in the axial direction. Thus, the set screws provide a means for adjusting the position of the cuvette ring bearings 64 while the cuvette ring bearings 64 provide a means for preventing the cuvette ring 62 from moving out of round and/or wobbling with respect to the magnet ring 66. The cuvette ring bearings 64 thus allow the cuvette ring 62 to slide freely about the magnet ring 66 while still insuring that the cuvette ring 62 is firmly secured to the magnet ring 66.

Although in this particular embodiment the cuvette ring 62 is movably coupled to the magnet ring 66 via the cuvette ring bearings 64, it is recognized that any means for movably coupling the cuvette ring 62 to the magnet ring 66 may also be used. It should be appreciated that the cuvette ring 62 and magnet ring 66 in fact need not be physically coupled together as long as the two rings can be accurately moved and positioned relative to each other.

Examples of other techniques which may be used to provide a cuvette ring and a magnet ring which are movable with respect to each other will be discussed below in conjunction with FIGS. 10–13.

During assembly, the magnet ring bearing 68 is first disposed over the base ring 70 and located in a particular position with respect to the base ring 70 via an alternating sequence of locating pins 72 and screw holes 74 which here are equally spaced around the perimeter of the base ring 70. The ring bearing 68 is provided having corresponding through holes 76 disposed to accept the locking pins 72 and allow the ring bearing 68 to be fastened to the base ring 70 via screws or other fastening means (not shown).

The magnet ring 66 is then press fit onto the ring bearing 68. To insure an accurate press fit, the magnet ring 66 and ring bearing 68 are manufactured having a filed interference fit. It should be noted that in alternate embodiments, the magnet ring 66 and ring bearing 68 could, of course, be provided as a single piece in which case the magnet ring 66 would form the outer race of the assembly.

The cuvette ring 62 and the cuvette ring bearing 64 are then coupled to the assembly formed by the magnet ring 66, magnet ring bearing 68 and base ring 70. The chamber covers 60 are then disposed over the entire ring assembly 90 to form the incubation chamber 12.

As mentioned above, in this particular embodiment the cover 60 is provided from a plurality of sub-covers 60a–60g. Sub-cover 60a corresponds to a back area cover, sub-cover 60b corresponds to a servo area cover, sub-cover 60c corresponds to a sample area cover, sub-cover 60d corresponds to a wash area cover, sub-cover 60e corresponds to an index area cover, sub-cover 60f corresponds to a reagent probe area cover and sub-cover 60g corresponds to a luminometer area cover. By providing the cover 60 from a plurality of sub-covers 60a–60g one can access different regions of the incubation chamber 12 without disturbing other regions of the incubation chamber 12. For example, in the event that the index mechanism 16 (FIG. 1) requires maintenance, the index cover 60e may be removed without disturbing the wash area cover 60d or any other covers. It is preferable, of course, if the dimensions of each of the chamber covers 60a–60g are selected to be equal to thus reduce the manufacturing costs and complexity of the chamber covers 60.

The sample area cover 60c is provided having a pair of slots 61a, 61b in a bottom surface thereof. The slots 61a, 61b allow the belt 35 (FIG. 1) and sensors (not shown) to be disposed in the incubation chamber. The sample area cover 60c also has a hole 61c provided in a top surface thereof. The hole 61c allows a sample probe to access a cuvette in the cuvette ring 62. It should be noted that each of the sub-covers may be provided having slots and holes therein to thus accommodate probes, sensors or any other devices which require access to the inside of the incubation chamber.

The wash separation cover 60d includes a pair of windows 82 through which a user operator can view the paramagnetic particle separation step of any particular assay cycle.

Each of the covers 60a–60g are preferably provided from a thermally conductive material such as aluminum to thus provide good thermal transfer characteristics with the base ring 70. Alternatively, the covers 60a–60g could be provided from plastic. One problem with the plastic cover approach, however, is that the incubation chamber 12 may have resultant warm regions and cold regions due to the poor thermal conduction characteristics of plastic. It is not desirable when processing the assays to subject the assays to arbitrarily varying temperature zones within the incubation chamber 12. Thus in the event it was desirable to provide the sub-covers 60a–60g from a material which is a poor thermal conductor, such as plastic for example, a thermally conductive finish could be disposed over the material to thus provide the incubation chamber 12 having relatively even thermal characteristics.

After each of the covers are disposed over the ring assembly and are secured to the base ring 70 via screws, an insulation cover (FIG. 6) is disposed over the entire assembly. The insulation cover may be provided, for example, as a one piece-vacuum form cover to thus reduce cost and facilitate assembly.

Figure 3:
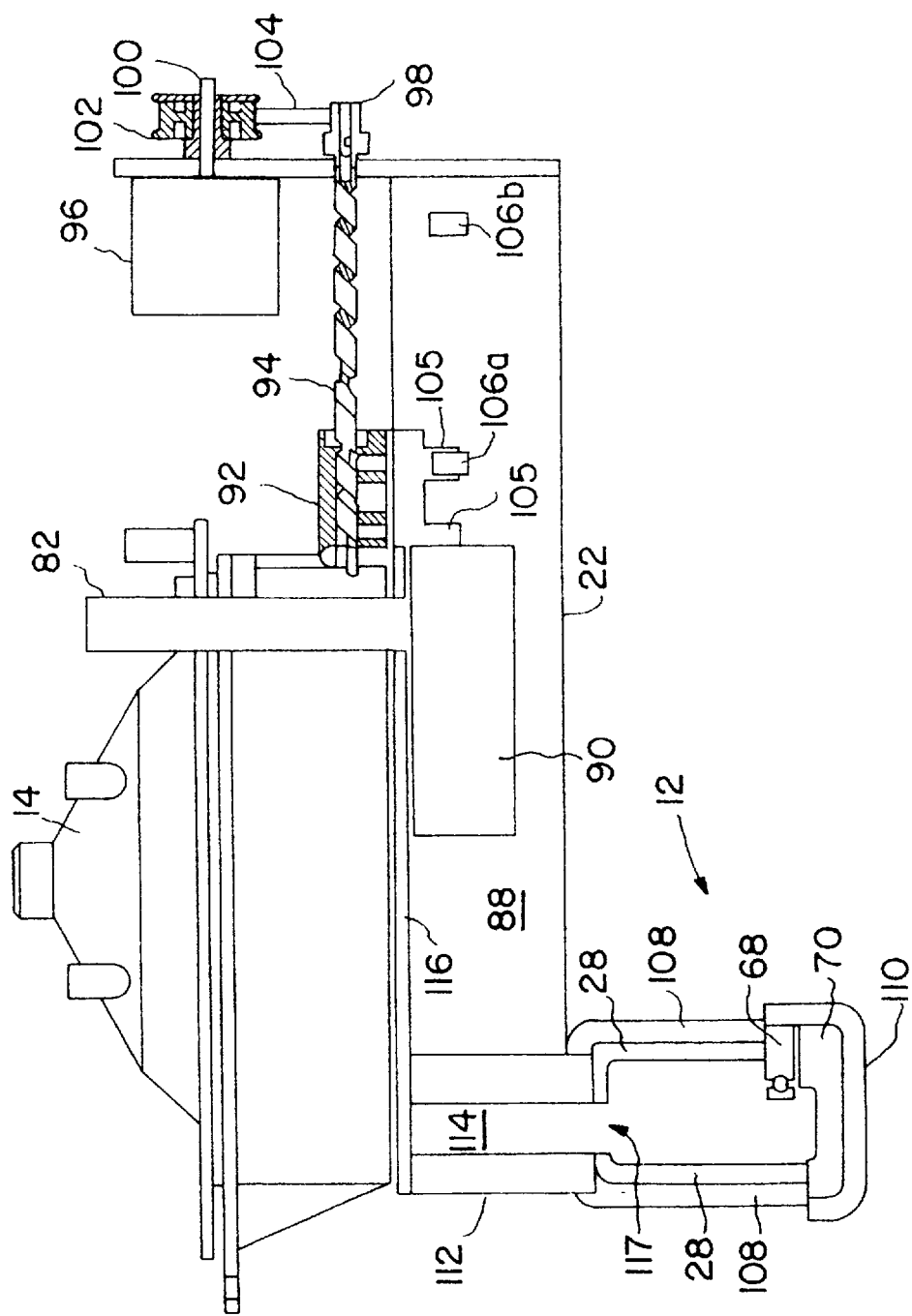
FIG. 3 is a cross sectional view of a preheat chamber region of an incubation chamber.

Referring now to FIG. 3, the preheat chamber 22 includes a preheat chamber entrance chute 82 through which cuvettes 84 are disposed into an entrance position of a first channel region 88 of the preheat chamber 22.

Cuvettes 84 are disposed in the entrance chute 82 and rest upon a first surface of a pusher block 90 here shown in a fully extended position. The pusher block 90 is coupled through a follower block 92 and lead screw 94 to a drive system 96 which may be provided from a stepper motor for example. The first end of the lead screw 94 has a lead screw pulley 98 coupled thereto. The drive system 96 includes a shaft 100 having a drive-shaft pulley 102 coupled thereto.

A belt 104 is coupled between the lead screw pulley 98 and the drive-shaft pulley 102. The drive system 96 turns the lead screw 94 in first and second opposite directions to thereby move the follower block 92 in first and second opposite directions along the length of the lead screw 94 and thus move the pusher block 90 in first and second opposite directions along the length of the preheat channel.

The follower block 92 has a pair of tabs 105 extending from a bottom surface thereof. The tabs 105 interact with a pair of optical sensors 106a, 106b which sense the position of the pusher block 90 and feed positioned information to the control system 25 (FIG. 1). When the pusher block 90 retracts past an opening in the top of the preheat chamber 22, a cuvette 84 falls through the opening and into the channel 28 of the preheat chamber 22.

The pusher block 90 pushes the cuvette 84 from the entrance position directly under the entrance chute 82 along the channel region 88 until the cuvette reaches an incubation chamber 12 entrance chute 114.

The incubation chamber 12 is here shown to include the cover 50, the base ring 70 and the magnet ring bearing 68 which are coupled to form a closed channel in which the cuvette 84 is disposed. The cuvette ring 62 (FIG. 2) and magnet ring 66 (FIG. 2) have been omitted for clarity. Disposed around the cover base ring and magnet ring bearing 68 of the incubation chamber 12 are a pair of insulating members 108, 110. The insulating members 108, 110 are here provided from a closed cell foam material having a thickness typically of about 0.25 inches. Other materials having similar insulation characteristics may of course also be used. The incubation chamber cover 28 and base ring 70 are provided from aluminum.

An end cap 112 forms the cuvette entrance chute 114 from the preheat chamber channel region 28 into the incubation chamber 12. The cuvette 84 travels through the cuvette entrance chute 114 through an aperture 117 of the incubation chamber 12 and seats in a slot of the cuvette ring 62 (FIG. 2).

The cuvette slots should be provided having a shape selected to accommodate the shape of the cuvette 84 such that the cuvette 84 can easily be accepted therein without having any surfaces that tend to bind or catch on a surface of the cuvette 84. Moreover, the cuvette slot should be provided having a shape which positions the cuvette 84 and holds the cuvette 84 relatively securely in the cuvette ring 62. The shape of the cuvette slot should also be selected such that cuvettes 84 can fall freely from the entrance chute 114 into the cuvette slot in a self guiding manner. Additionally the cuvette slot should be provided having a shape that could be manufactured relatively inexpensively.

The preheat channel 88 has disposed thereover an acrylic cover 116 having a thickness typically about 0.25 inches which provides the preheat chamber 22 as a closed channel and also serves to insulate the preheat chamber 22 from other surfaces contacting the top portion of the preheat chamber 22.

As may be more clearly seen in FIG. 1, in this particular embodiment the entrance from, the preheat chamber 22 to the incubation chamber 12 is spaced a relatively short distance from the luminometer 14 and in particular from the luminometer entrance chute 114. Those of ordinary skill in the art will recognized of course that the cuvette entrance from the preheat chamber 22 to the incubation chamber 12 could be disposed at any region of the incubation chamber 12.

It is convenient in this particular embodiment, however, to position the cuvette entrance chute 114 proximate the luminometer 14 since the luminometer 14 provides a means for removing cuvettes 84 from the incubation chamber 12 and from the analyzer system 10. That is, a cuvette 84 can be moved from the cuvette ring 62 into the luminometer 14. The luminometer 14 measures the amount of light emitted from a chemiluminescent reaction which takes place in the cuvette 84. Upon completion of the measurement, the luminometer 14 expels the cuvette 84 in which the reaction took place from the analyzer system 10 (FIG. 1).

It should be noted that since the magnet ring and cuvette ring can move in both clockwise and counter clockwise directions there is a great deal of flexibility with respect to the particular placement of devices such as the probes 24, the luminometer 14, the index mechanism 16 and the cuvette entrance chute 22 about the incubation chamber. The devices, however, must be placed to allow certain processes to take place at predetermined periods of time and thus must be selected in accordance with the motions of the cuvette and magnet rings. Exemplary motions of the cuvette and magnet rings will be described in conjunction with FIGS. 8–8b below.

Figure 4:
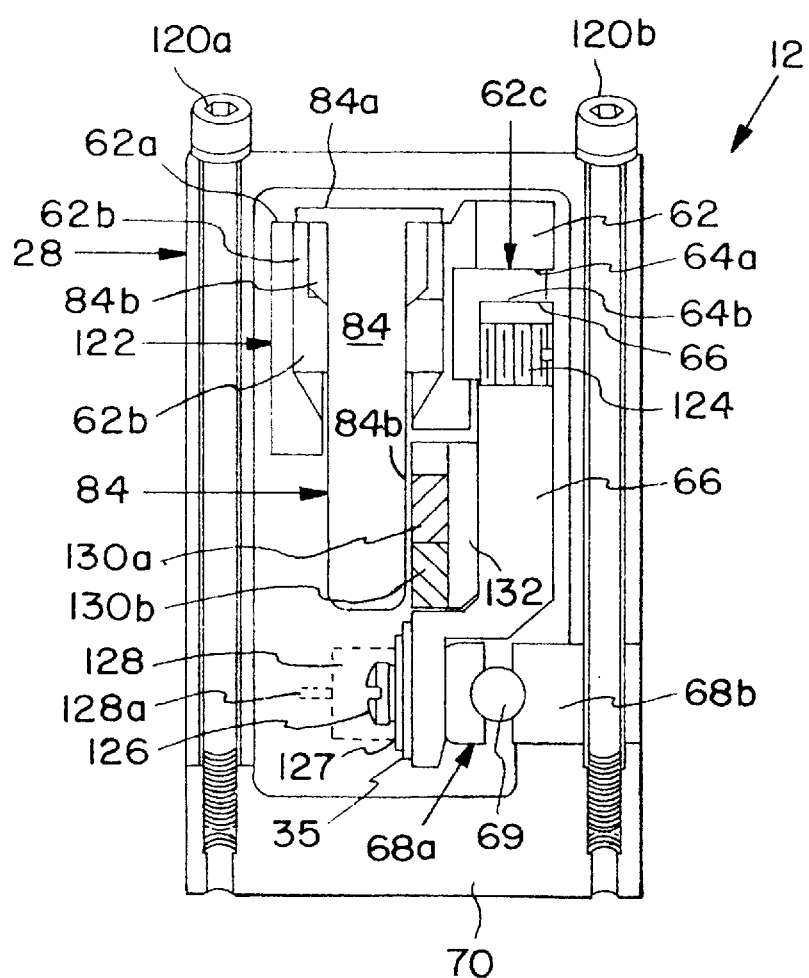
FIG. 4 is a cross sectional view of an incubation chamber.

Referring now to FIG. 4, the incubation chamber 12 includes the cover 60 and base 70 here coupled together via screws 120a, 120b. It should be noted, however, that any type of fastening technique well known to those of ordinary skill in the art may also be used to secure together the cover 60 and base ring 70 portions of the incubation chamber 12.

A cuvette 84 is shown disposed in a cuvette slot 122 of the cuvette ring 62. The cuvette 84 is provided having a top flange 84a, which rests on shoulder region 62b of the cuvette ring 62 and a side flange 84b which engages side wall regions of the cuvette ring 62 which form the cuvette slot 122.

A first surface of a cuvette ring 62 is disposed against a first surface of a cuvette ring bearing 64. A second surface of the cuvette ring bearing 64 is disposed against a first surface of the magnet ring 66. As described above, the cuvette ring bearing 64 is held in place by a pair of screws and an adjustable set screw 124. The cuvette ring bearing 64 thus secures the cuvette ring 62 in a predetermined axial position relative the magnet ring 66.

The magnet ring 66 is coupled via a press fit to an outer race of the magnet ring bearing 68. The magnet ring bearing 68 also includes an inner race spaced from and movably coupled to the inner race by a ball bearing 69. The ball bearing 69 allows the outer race to move relative the inner race as is generally known.

A screw 126 and washer also secures a first end of the metal drive belt 35 to the magnet ring 66. A second end of the drive belt 35 is similarly fixed to the magnet ring 66. Thus, first and second ends of the drive belt 35 are pinned to the magnet ring 66 at predetermined locations.

In preferred embodiments a member 128 here shown in phantom, projects from the magnet ring 66 in the region where the belt 35 terminates with respect to the ring 66. The member 128 has projecting therefrom a fin 128a having a radial shape which interrupts a sensor such as an optical sensor when the magnet ring 66 has moved as far as possible in one direction. Upon start up of the system 10, the servo motor 18 drives the magnet ring 66 slowly in one direction until the fin 128a interrupts the optical sensor thus indicating that the belt cannot allow the magnet ring to turn any further in that direction. This technique is used to initialize an encoder coupled to the servo motor 18 and allows the encoder to determine start and end positions of the magnet ring 66.

Also, in the event that the encoder coupled to the servo motor fails, the sensor flag and optical sensor arrangement can act as a fail safe mechanism. If the servo motor attempts to drive the magnet ring past a predetermined point in a single direction, the sensor sends a signal to initiate shut down of the servo motor and thus prevents the magnet ring or the drive belt from being broken. Furthermore, a physical stop may be disposed to engage the member 128 and prevent the magnet ring from advancing too far in one direction in the event that both the encoder and optical sensor fail to operate properly.

The magnet ring 66 thus turns in response to movements of the drive belt 35. Since the drive belt 35 is pinned to the magnet ring 66, it is not possible for the magnet ring 66 to rotate in a single direction for a distance greater than 360 mechanical degrees. That is, in this particular embodiment, the magnet ring 66 cannot continuously spin in any one direction.

However, by pinning the drive belt 35 to the magnet ring 66 it possible to accurately position the magnet ring 66 and thus each of the cuvette slots in the cuvette ring 62 at particular locations around the incubation chamber 12. Furthermore, by providing the belt 35 as a steel belt 35 such positioning accuracy can be further increased since the steel belt 35 will have very little stretch and very low backlash.

It is desirable to have the capability of accurately positioning each of the cuvettes 84 disposed in the cuvette ring 62 since the cuvettes 84 must be accurately positioned to allow pipettes at each of the fixed probe stations 24 (FIG. 1) to be lowered into the cuvettes 84 for dispensing and aspiration of fluids. Thus to enable the drive system 18 (FIG. 1) to accurately position each of the cuvettes 84, the metal drive belt 35 is pinned to the magnet ring 66. In an alternate embodiment, the magnet ring could be provided having teeth similar to the drive pulley which engages holes in the metal belt.

It is also possible of course that rather than pinning the drive belt 35 to the magnet ring 66 via the screw 126, a friction coupling between the drive belt 35 and the magnet ring 66 could be used. With this approach the magnet ring 66 would of course be able to turn continuously in a single direction for multiple revolutions. It should be noted, however, that even in the case where a friction coupling between the drive belt 35 and the magnet ring 66 is provided, it is still preferable to use a steel drive belt to minimize stretching and backlash of the drive belt which would result in inaccuracies in turning the magnet ring 66 and positioning cuvettes 84 at predetermined locations of the incubation chamber 12. It should also be noted that in this approach, a thin layer of polyurethane or rubber may be applied to either (or both) the magnet ring or the belt to further increase the coefficient of friction between the belt and the ring.

It should also be noted that in this particular embodiment the drive unit 18 is provided as a servo motor capable of very accurately turning the drive belt 35 and thus the magnet ring 66.

The incubation chamber 12 further includes a magnet pair 130 provided from magnets 130a, 130b coupled to the magnet ring 66 via a mounting plate 132. The magnet pair 130 and mounting plate 132 will be described in detail below in conjunction with FIG. 5. Suffice it here to say that as described above in conjunction with FIG. 1, as the cuvette 84 passes by the magnets 130a, 130b the magnets attract and hold paramagnetic particles disposed in the cuvette 84 to a first surface of the cuvette 84b proximate the magnets 130a, 130b. In this manner the paramagnetic particle separation portion of the assay is achieved.

Figure 5:
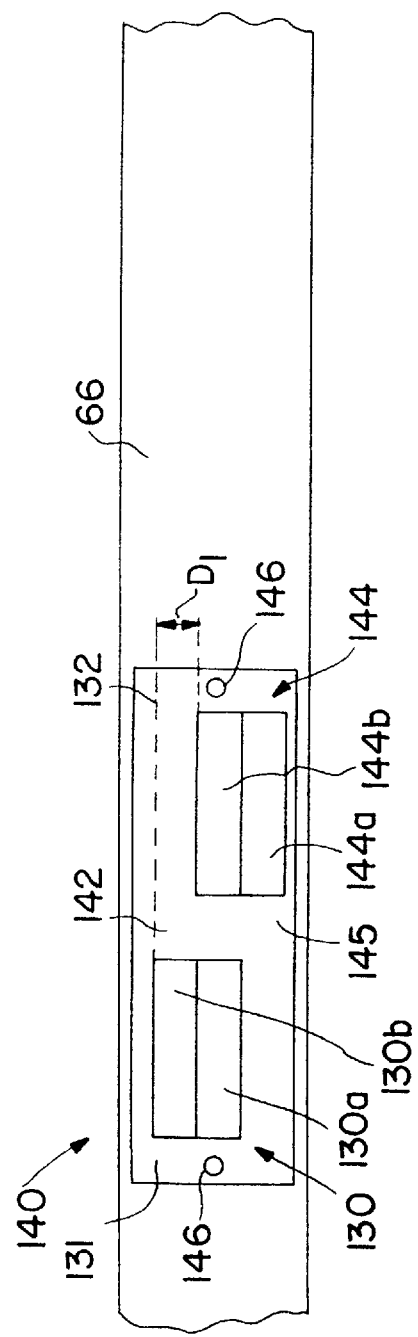
FIG. 5 is a side view of a split magnet assembly.

Referring now to FIG. 5, a split magnet assembly 140 includes the magnet pair 130a, 130b, generally denoted 130 separated by a spacer 142 a predetermined distance from a second pair of magnets 144a, 144b, generally denoted 144. The magnet pairs 130, 144 are offset in a vertical direction by a predetermined distance D1 to facilitate the paramagnetic particle separation procedure.

The magnet pairs 130, 144 are secured to a magnet mounting plate 132 which in turn is secured to the magnet ring 66. In one embodiment the magnet pairs 130, 144 are secured to the mounting plate 132 by providing the mounting plate 132 from a magnetically attractive material such as steel and allowing a magnetic force to hold the magnet pairs 130, 144 to the mounting plate 132. Alternatively the magnet pairs 130, 144 may be secured to the mounting plate 132 via an epoxy or by any other fastening technique well known to those of ordinary skill in the art. In cases where a magnetic force is not used to couple the magnet pairs 130, 144 to the magnet plate 106, the magnet plate 106 need not be provided from a magnetically attractive material.

In this embodiment a pair of bolts 146 secure the mounting plate 132 to the magnet ring 66. It should be noted, however, that the mounting plate 132 may be attached to the magnet ring 66 using epoxy or any other fastening technique well known to those of ordinary skill in the art. In some embodiments, however, it may be preferable to omit the mounting plate 132 and mount the magnet pairs 130, 144 directly to the magnet ring 66.

The magnet pairs 130, 144 are here selected having equal lengths. Each of the magnet pairs 130, 144 spans a distance covering six cuvette slots in the cuvette ring 62. Thus, six cuvettes 84 can be positioned in front of each of the magnet pairs 130, 144 at any time. By spacing the magnet pairs 130, 144 and performing a particle re-suspension operation in a cuvette 84 positioned in the space between the magnets, it is possible to improve the results of some assays and in particular it is possible to improve the results of some ID assays. It should be noted that the magnet pairs 130, 144 could of course be provided having a longer or a shorter length and that in some applications the magnet pairs 130, 144 could be provided having different lengths.

The particular length of each of the magnet pairs 130, 144 is selected based, inter alia, on the amount of time it is desired to expose an assay to a magnetic force. Thus assuming that it is desired to expose an assay to a magnetic force for a predetermined period of time, if the cuvettes 84 are moved past the magnet pairs 130, 144 at a first predetermined speed, the magnet pairs 130, 144 should be provided having a first length. If the cuvettes 84 are moved past the magnet pairs 130, 144 at a second slower speed, however, then to expose the assay to the magnet pairs 130, 144 and magnetic force for the same predetermined period of time, the magnet pairs 130, 144 should be made shorter such that the assays are positioned in front of the magnets for a shorter distance but for the same predetermined period of time. Thus suffice it to say that the particular length of the magnet pairs 130, 144 should be selected in accordance with a variety of factors including but not limited to the speed with which cuvettes 84 pass by the magnets and the amount of time required to ensure proper paramagnetic particle separation in the cuvette 84.

It should also be noted that in this particular embodiment a first end of a first one of the magnet pairs 130, 144 is spaced by a distance typically about the length of a single cuvette from a first end of second one of the magnet pairs 130, 144. Thus, a single cuvette 84 can be positioned in front of the spacer region and thus not be subject to the magnetic forces of the magnets. It is recognized, of course, that in some applications it may be desirable to space the magnet pairs 130, 144 by a distance which is greater than one cuvette. Alternatively, it may be desirable in some applications to not space the magnets at all but rather to couple the magnets adjacent to each other on the mounting plate 132.

It should also be noted that the magnets 130a, 130b, 144a, 144b are preferably provided having a shape corresponding to the shape of the surface of the magnet ring 66 to which the magnets are coupled. In this particular embodiment, the magnet ring 66 is provided having a circular shape. Thus as may be more clearly seen in FIG. 1, the magnets are provided having a curvature corresponding to the curvature of the magnet ring 66.

Those of ordinary skill in the art will appreciate that it is relatively difficult to manufacture magnets having a curved shape and that such curved magnets are relatively delicate and can be easily broken. In some applications it may therefore be desirable to provide the individual magnets 130a, 130b, 144a, 144b from a plurality of individual magnet segments which are juxtaposed to form the overall curved magnet assemblies 130, 144. The juxtaposed individual magnet segments may either be adjacent or spaced depending upon the particular application. The particular number of individual magnets or magnet segments which comprise each of the magnet assemblies 130, 144 should preferably be selected to, inter alia, minimize fabrication cost while providing relatively robust magnet assemblies 130, 144.

By vertically offsetting the magnet pairs 130, 144, the paramagnetic particles are gathered from both the upper and lower portions of the cuvette and are eventually focused into a pellet along the center of the lower magnet pair 144. As the cuvette 84 moves past the magnet pair 130 paramagnetic particles collect along the entire magnet pair 130 surface. A wash operation is then performed to remove non-bonded particles within the cuvette 84. Then as the cuvette 84 moves past the magnet pair 144 paramagnetic particles are further focused into a pellet along the center line of the lower magnet pair 144. With this technique a focused pellet is formed from particles gathered across the entire cuvette 84. The distance between the lowest edge 145 of magnet pair 144 and the highest edge 131 of the magnet pair 130 is, in this embodiment, selected to be less than the length of the fill volume of the cuvette 84.

Figure 6:
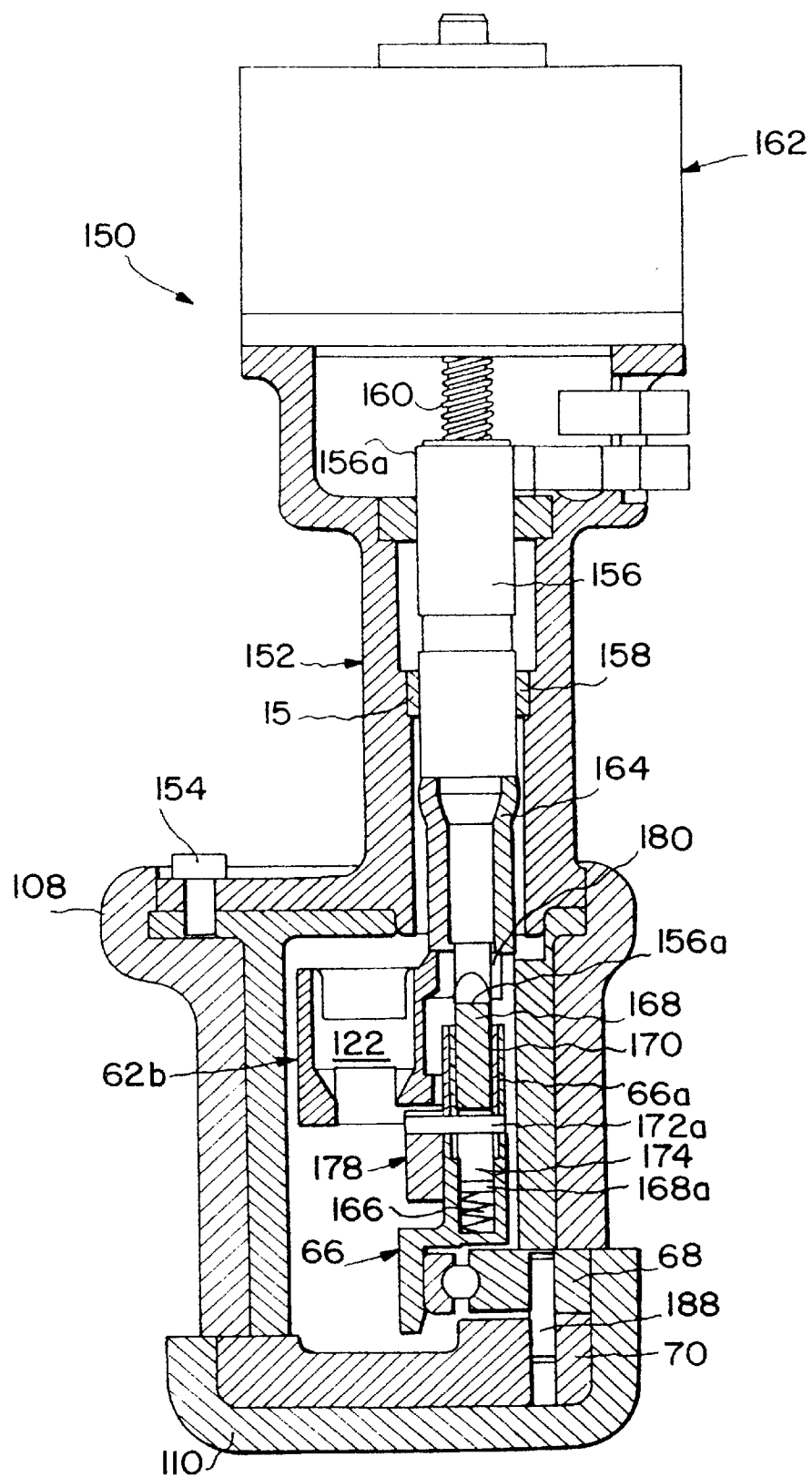
FIGS. 6 and 6A are cross sectional views of an index mechanism.

Referring now to FIG. 6, an index mechanism 150 includes an index housing 152 coupled to the incubation chamber 12 cover via several bolts 154 one of which is shown here. An index plunger 156 disposed through a bore in the index housing 152 and is located in the housing bore by a guide bearing 158. A first end 156a of the index plunger 156 is coupled to a lead screw 160. The lead screw 160 is coupled to a linear drive motor 162 which is here provided as a stepper motor. The guide bearing 158 allows the index plunger 156 to move up and down through the bore in the index housing 152 in response to movements of the motor 162 and drive shaft 160.

A clamp foot 164 is disposed about a second end of the plunger 156. The clamp foot 164 may be provided, for example, from a piece of rubber tubing having a predetermined durometer hardness.

A bore 174 of the magnet ring 66 has disposed therein a detent spring 166 and a first end of a stainless steel detent pin 168. A guide bushing 170 is disposed in the slot to prevent the detent pin 168 from wearing down the magnet ring walls. The guide bushing 170 may be provided, for example, as an oil impregnated bronze bushing. As the bushing walls wear down, the bushing 170 leaches out lubricant and thus the bushing 170 acts as a self lubricating bushing. Those of ordinary skill in the art will appreciate of course that other wear resistant materials and techniques for reducing or minimizing wear between two moving surfaces could also be used.

A retainer pin 172 is disposed through a slot in the detent pin 168. A first end of the retainer pin 172 is coupled to a first wall 66a of the magnet ring 66. A second end of the retainer pin 172 is disposed through a hole in a second wall of the magnet ring 66 and coupled to a retainer block 178.

Figure 6A:
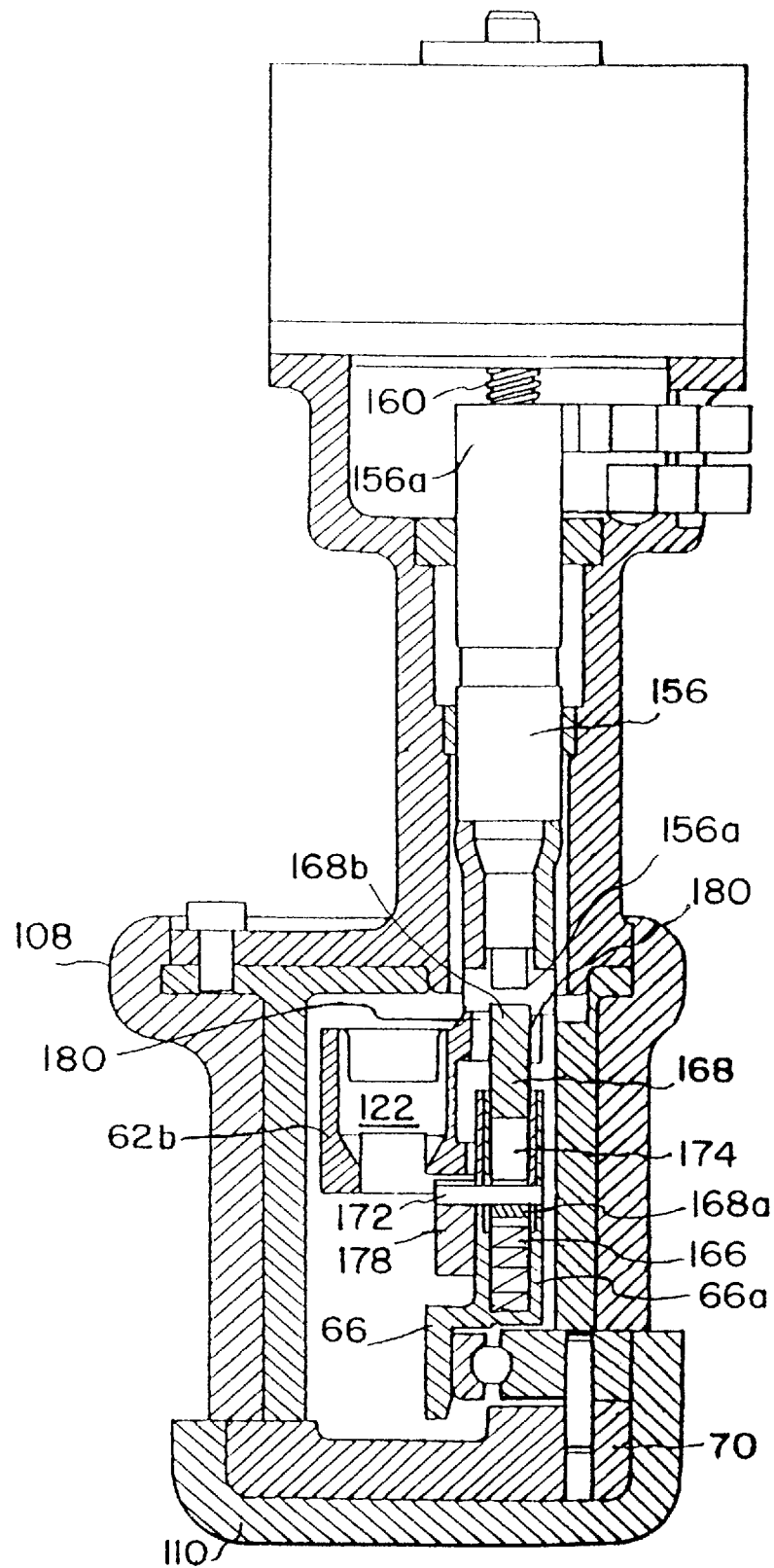

Referring briefly to FIG. 6A in which like elements of the index mechanism 150 are provided having like reference designations, when the index plunger 156 is in its up position as shown in FIG. 6A, the detent pin 168 is placed in its detent position. In its detent position, the first end 168a of the detent pin 168 remains coupled to the magnet ring 66 as described above. The detent spring 166 forces a second end 168b of the detent pin 168 through a slot formed in wall region 180 in the cuvette ring 62. Thus in its detent position, the detent pin 168 engages the cuvette ring 62 and locks the cuvette ring 62 to the magnet ring 66 thereby preventing the cuvette ring 62 from moving relative to the magnet ring 66.

Thus, with the detent pin 168 in its detent position, the cuvette ring 62 moves with the magnet ring 66. Additionally, when the cuvette ring 62 is locked to the magnet ring 66 via the detent pin 168, the position of the magnet pairs 130, 144 (FIG. 5) is fixed with respect to cuvettes 84 held in the cuvette ring 62.

Referring again to FIG. 6, the detent pin 168 is shown disengaged from the cuvette ring 62 thereby unlocking the cuvette ring 62 from the magnet ring 66. When the detent pin 168 is disengaged, the cuvette ring 62 is movably uncoupled from the magnet ring 66. That is, the cuvette ring 62 can move on the cuvette ring bearings 64 (FIG. 4) relative to the magnet ring 66

The detent pin 168 is disengaged from the cuvette ring 62 in the following manner. In response to the motor 162 moving the lead screw 160 in a downward direction in the bore of the index housing 152, a first surface 156b of the second end of the index plunger 156 contacts a first surface of the detent pin 168 and drives the detent pin 168 against the detent spring 166 until the detent pin 168 is pushed completely through the slot in the cuvette ring 62. At this point, the cuvette ring 62 is de-coupled from the magnet ring 66 and can therefore move relative to the magnet ring 66.

The slot in the detent pin, through which the retainer pin 172 is disposed, is provided having a length selected to allow the detent pin 168 to be pushed down against the detent spring 166 a distance sufficient to allow the detent pin 168 to pushed through the detent slot in the wall region of the cuvette ring and below the surface of the cuvette ring 62 before the retainer pin 172 bottoms against a surface of the detent pin 168 in the slot region 174 of the detent pin 168.

Since the retainer pin 172 has a force exerted on it each time the magnet ring 66 indexes with respect to the cuvette ring 62, it is desirable to ensure that the retainer pin 172 is firmly secured to the magnet ring 66. In this particular embodiment, the walls of the magnet ring 66 through which the retainer pin 172 is disposed are not thick enough to properly support the retainer pin 172. Thus, the retainer block 178 is coupled to the magnet ring 66 to add support to the retainer pin 172. The retainer block 178 can be fixed to the magnet ring 66 by screws, epoxy, or by any other fastening techniques well known to those of ordinary skill in the art.

It should be noted that when the detent pin 168 is forced against the detent spring 166 by the index plunger 156, a first surface of the clamp foot 164 contacts a surface of the cuvette ring 62 in the region of the cuvette ring 62 in which the slot is formed. When the cuvette ring 62 is disengaged from the magnet ring 66, the steel belt 35 and drive assembly advance the magnet ring 66 in a clockwise direction to thus move the magnet ring 66 including the index pin relative the cuvette ring 62. Thus, during the index operation the cuvette ring 62 remains stationary and the magnet ring 66 advances the magnet pairs 130, 144 one cuvette position.

The cuvette ring 62 has a plurality of like detent slots formed therein. The detent pin 168 can engage each of the like detent slots in the cuvette ring 62. Each detent slot in the cuvette ring 62 defines a relative position between the cuvette slots in the cuvette ring 62 and the magnet pairs 130, 144 coupled to the magnet ring 66.

During an indexing operation, the detent pin 168 slides off the surface 156b of the index plunger 156 and moves along a bottom surface of the cuvette ring 62 until the detent pin 168 is aligned under the next detent slot in the cuvette ring 62. When the detent pin 168 is aligned with a detent slot, the detent spring 166 forces the detent pin 168 through the detent slot to again couple the cuvette ring 62 to the magnet ring 66. Thus when the magnet ring 66 advances a predetermined distance, here corresponding to one cuvette slot, the detent pin 168 is forced by the spring 166 into the next available detent slot of the cuvette ring 62 to thus re-secure the cuvette ring 62 to the magnet ring 66. The detent pin 168 and the slots in the wall 180 of the cuvette ring 62 constitute an escapement and the plunger 156 of the index mechanism 150 constitutes a trigger for the escapement.

While the detent pin 168 is being indexed, the detent pin 168 and detent spring 166 exert a force on the bottom surface of the cuvette ring 62. The clamp foot 164 provides a force against a top surface of the cuvette ring 62 to counteract the force exerted by the detent pin 168 and detent spring 166. Additionally, the clamp foot tubing reduces flexing and dampens any oscillation of the cuvette ring 62 which occurs due to the index pin being forced into the detent slot of the cuvette ring 62.

It should be noted that although in this particular embodiment the detent pin 168 locks the cuvette ring 62 to the magnet ring 66, other locking means may also be used. Likewise, although an index plunger 156 is used to disengage the cuvette ring 62 from the magnet ring 66 other disengaging means may also be used. For example, the detent pin 168 and index plunger 156 arrangement could be replaced by a solenoid for example.

Figure 10A:
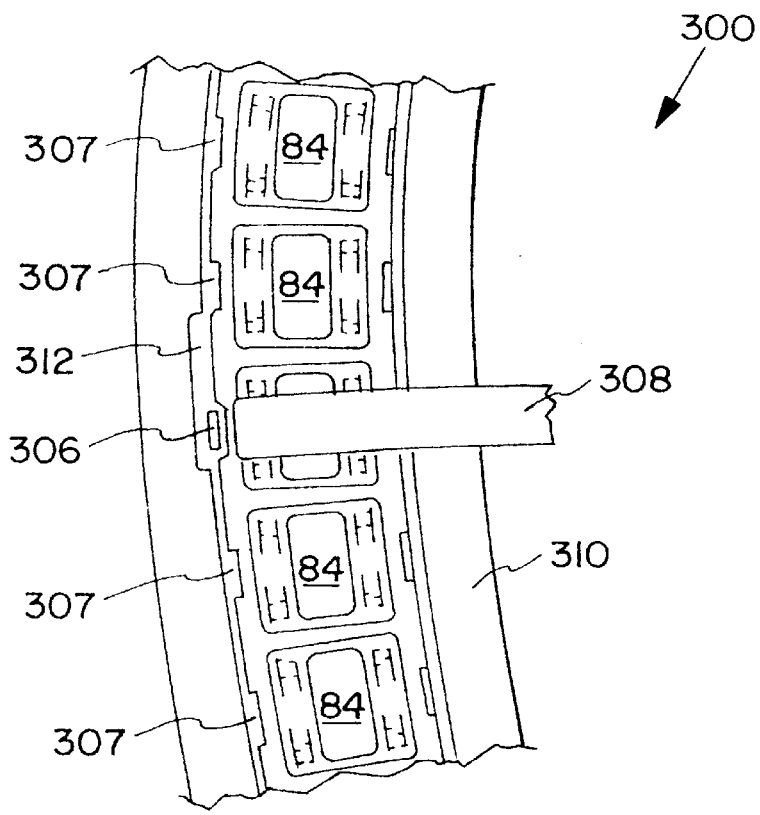
FIGS. 10 and 10A show an alternate embodiment of an incubation chamber having separately movable cuvette and magnet rings.
Figure 10:
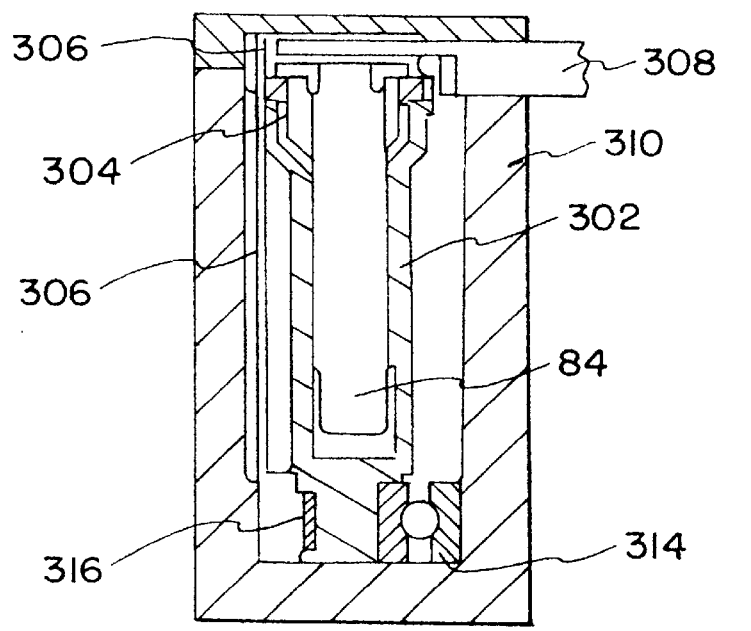

Other techniques for providing the cuvette ring 62 and the magnet ring 66 as engageable, movable rings will be discussed in conjunction with FIGS. 10–12 below. Thus, suffice it to say that the cuvette ring 62 and magnet ring 66 may each include engageable locking regions which interact to thereby selectively lock the cuvette ring 62 and magnet ring 66. It should, however, be noted that in some embodiments the cuvette ring 62 and magnet ring 66 may not include locking regions but rather may simply move independently of each other to thus move the magnets pass the cuvettes.

As mentioned above, in this particular embodiment, the rubber tube clamp foot 164 contacts the cuvette ring 62 to provide a downward force to counteract the upward force provided from the spring and detent pin 168 and spring and thereby minimize movement of the cuvette ring 62 in a vertical direction.

In an alternate embodiment, the rubber tube clamp foot 164 could be replaced by a foot spring and clamp foot arrangement for example. The foot spring should be selected having a spring force to dampen and counteract the forces which arise when the detent pin 168 is pushed by the spring against the cuvette ring 62. In this case, a shoulder region of the index plunger 156 compresses the foot spring against the clamp foot to thus counteract the force which the detent pin 168 exerts on the cuvette ring 62 surface due to the upward force provided by spring 166. Those of ordinary skill in the art will now appreciate that other means for dampening and counteracting the forces which arise while indexing the cuvette ring 62 relative to the magnet ring 66 can also be used.

The index plunger 156 and detent slot in the cuvette ring 62 are provided having tolerances to ensure that in a worst case tolerance scenario (i.e. the index plunger 156 having a maximum diameter and the index slot having a minimum diameter) the index plunger 156 will not be provided having a diameter greater than the diameter of the detent slot. The nominal clearance between the second end of the index plunger 156 and the index slot is typically about 0.003 inches. Such a relatively tight clearance prevents the cuvette ring 62 from shifting position while the index operation is taking place. It is desirable to prevent any cuvette ring 62 movement from occurring during the index operation since other operations may simultaneously be taking place. For example, sample, reagent or wash probes may be entering cuvettes 84 during the index operation.

With such relatively tight tolerances, the drive system 18 must position the cuvette ring 62 within several one-thousandths of an inch in order to ensure that the second end of the plunger can move through the detent slot. Thus, after the drive system 18 moves the cuvette ring 62 a predetermined number of positions in a predetermined time interval, for example, 53 positions in one second, the drive system 18 must be capable of stopping and positioning the cuvette ring 62 within several-thousandths of an inch of a predetermined position. In the event, however, that some misalignment occurs between the cuvette ring 62 and the index mechanism 150, the second end of the index plunger 156 can be provided having a tapered region to allow the index plunger 156 to accommodate some cuvette ring 62 misalignment which may occur.

As mentioned above, the drive system 18 includes a servo motor capable of accurately moving a predetermined distance. The drive system 18 also includes the metal drive belt 35 having a plurality of accurately spaced and sized holes provided therein. Moreover, teeth projecting from a drive pulley of the motor 18 which engage the holes in the metal drive belt 35 are positioned very accurately on the drive pulley to thus increase the accuracy with which the drive system 18 can position the magnet ring 66 and thus the 5 cuvette ring 62. With this particular servo motor, metal belt arrangement, backlash in the drive system 18 (i.e. the amount of play the drive belt 35 has as it engages a tooth on the drive motor pulley) is typically about 0.002 inches.

The base ring 70 and magnet ring bearing 68 are each provided having bores therein. An alignment pin having a first end disposed in the bore of the base ring 70 and having a second end disposed in the bore of the magnet ring bearing 68 provides a means for properly aligning the base ring 70 and the magnet ring bearing 68.

It should also be noted that although in FIGS. 6 and 6A gaps or spaces are shown between the base ring 70, the magnet ring bearing 68 and the magnet ring 66, such gaps are shown only to facilitate understanding of the assembly. Each of the above mentioned assemblies, in fact, are tightly fit to each other to thus prevent movement between each of the pieces. Because of the secure fit between each of the pieces, the magnet ring bearing 68 provides a thermal path through which heat generated by the thermal means coupled to the base ring 70 may be transferred throughout the incubation chamber 12.

Figure 7:
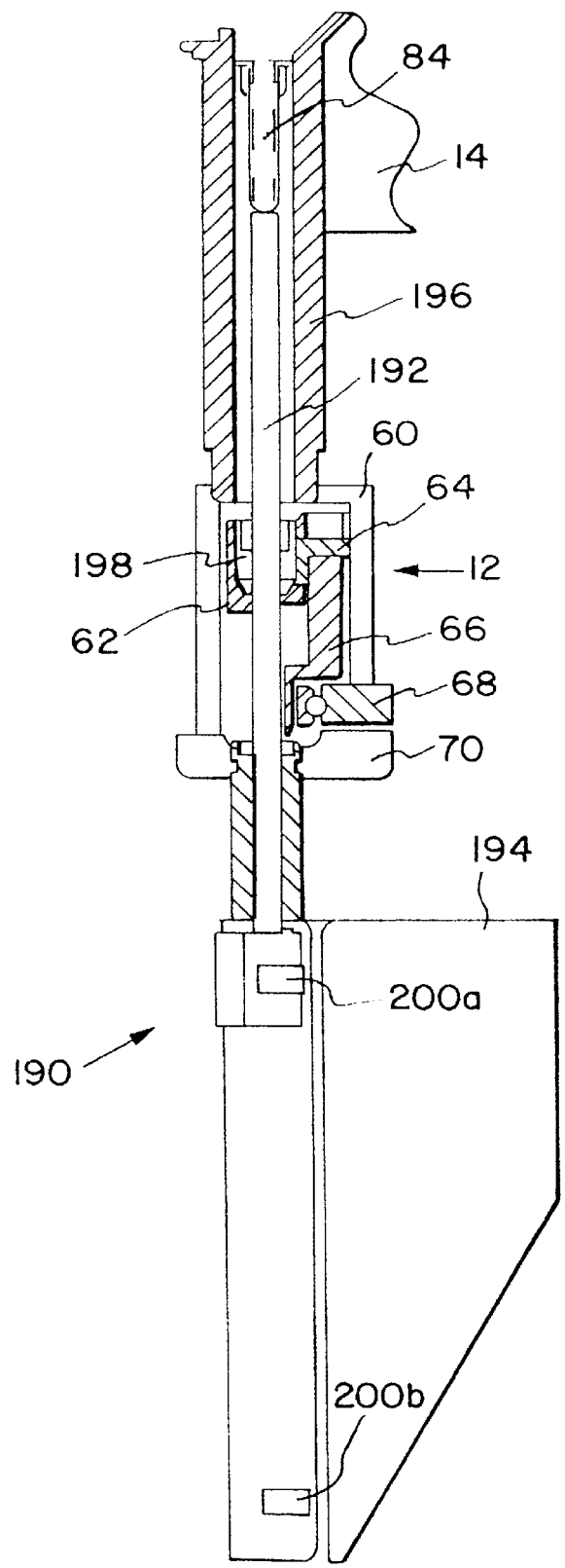
FIG. 7 is a cross sectional view of an elevator mechanism used in an incubation chamber.

Referring now to FIG. 7, an elevator assembly 190 includes a lift rod 192 and a drive assembly 194. The drive assembly 194 drives the lift rod 192 through a predetermined region of the incubation chamber 12 to thus lift a cuvette 84 through an entrance shaft 196 of the luminometer 14 only a portion of which is here shown. The elevator assembly 190 positions the cuvette 84 into a predetermined one of a plurality of cuvette chambers within the luminometer 14. In this manner, cuvettes 84 are removed from the incubation chamber 12 thus opening up a cuvette slot in the cuvette ring 62 to thus allow a new cuvette 84 to be placed into the cuvette ring 62.

Those of skill in the art will appreciate of course that in some applications it may not be necessary to pass the cuvette 84 from the incubation chamber 12 to a luminometer 14. Rather, the cuvette 84 may simply be ejected from the incubation chamber 12 at any convenient location and passed to a second different incubation chamber 12 or alternatively the cuvette 84 may be ejected and disposed of in any manner appropriate to the system in which the incubation chamber 12 is being employed.

In some applications, for example, it may be desirable or necessary to remove the cuvette 84 from the incubation chamber 12 through an opening provided in the bottom of the incubation chamber 12. In this case the elevator assembly 190 would not be required.

The elevator assembly 190 includes a pair of sensors 200a, 200b which sense the position of the lift rod 192 and thereby determine the position of the cuvette 84 in the elevator shaft. The sensors 200a, 200b send signals to the control system 25 (FIG. 1) to prevent the control system from turning the cuvette and magnet rings 62, 66 while the lift rod 192 is disposed through the incubation chamber 12. Once the elevator lift rod 192 retracts out of the incubation chamber 12, the sensor assemblies send a signal to the control system 25 which then allows the magnet and cuvette rings 62, 66 to begin moving again.

Figure 8B:
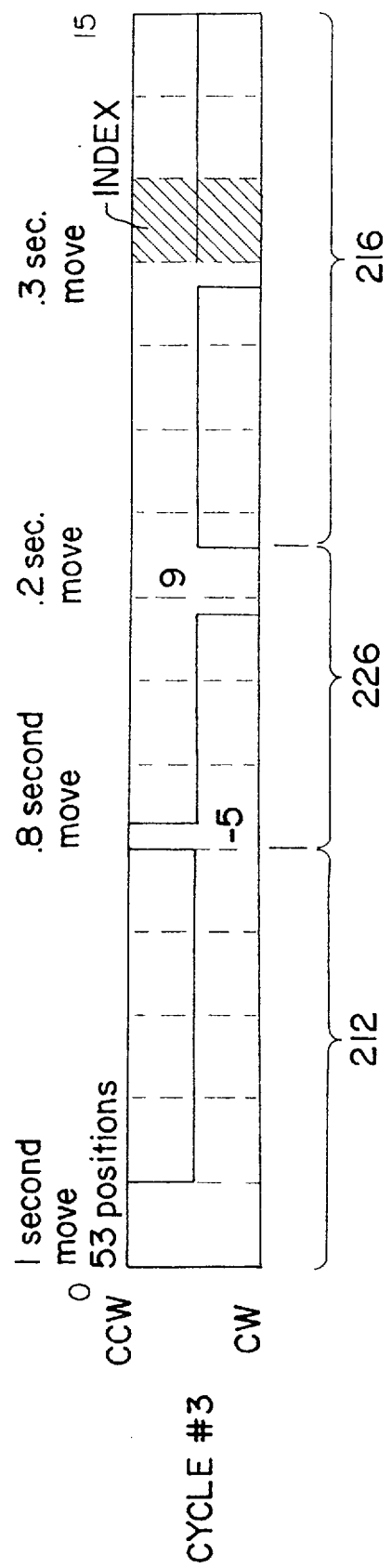

Referring now to FIGS. 8–8B, a series of diagrams illustrating the movements of the cuvette ring 62 and magnet ring 66 during three different system cycles is shown. It should be noted that these cycles are merely illustrative of the plurality of possible cycles which can be implemented in the system 10 and are not to be considered limiting with respect to the types of cycles which can be performed in the system 10.

Turning now to FIG. 8, a diagram illustrating the movements of the cuvette and magnet rings 62, 66 during a typical cuvette cycle 210 of the system 10 is shown. In the present embodiment, the cuvette cycle 210 is defined to have a 15 second time interval. It should be noted, however, that other cuvette cycle times can also be defined. The 15 second cuvette cycle is shown divided into 3 portions time frames 212, 214, 216. During each portion of the cuvette cycle, the cuvette ring 62 and magnet ring 66 are able to move in either clockwise or counter clockwise directions.

As shown in FIG. 8 the frame 212 of the cuvette cycle 210 lasts for a period of time corresponding to about 5 seconds. During the first second of the five second time frame 212, the cuvette ring 62 moves 53 positions in a counter clockwise direction around the incubation chamber 12.

During the remaining 4 seconds of the frame 212 the cuvette ring 62 does not move and one or more of the following operations can be performed.

First, primary reagents can be added to particular cuvettes. The particular type of assay being processed will determine the particular primary reagent which should be added as well as the incubation time of the assay. Some assays have incubation times typically of about eight minutes while other assays may have incubation times of about eighteen minutes. Furthermore, ancillary reagents (e.g. pretreatment or release reagents) used to prepare or dilute a sample for a particular test can also be added to particular cuvettes during this portion of the cycle.

Additionally, if any cuvettes are appropriately positioned in the wash/paramagnetic particle-separation region of the incubation chamber 12 (i.e. cuvette ring positions 8–20 as shown in FIG. 1) wash and re-suspension operations may take place during this portion of the cycle. Also if an appropriate cuvette is positioned at cuvette ring position number 6, an acid dispense into the cuvette may also take place. Thus suffice it to say that a plurality of different operations may take place at different process stations of the incubation chamber 12 during frame 212 of the cycle 210.

It should be noted, however, that whether a particular process actually occurs depends upon the positioning of cuvettes presently residing in the incubation chamber 12 as well as the particular assay being performed in the cuvettes. For example, even if a cuvette is positioned at the ancillary reagent dispense probe, if that particular cuvette does not require an ancillary reagent then no operation takes place in that cuvette at that particular time.

The movements of the cuvette which occur during the second frame 214 of the cycle depend upon the particular test being performed. For example, if an assay having an incubation period lasting for about 8 minutes is being dispensed then the cuvette ring 62 moves in a clockwise direction 39 positions such that a particular cuvette is positioned under the sample dispense probe. The 39 position move is accomplished in 0.8 seconds.

After positioning the cuvette, a new sample is dispensed from the sample dispense probe into the cuvette or a diluted sample previously aspirated may be dispensed into a new cuvette. The dispense must take place in a period of time typically about 2.5 seconds.

The cuvette ring 62 then moves clockwise 5 additional cuvette positions to position the cuvette under the ancillary dispense position. The 5 position movement is accomplished in 0.2 seconds. Thus the second frame 214 of the cycle 210 is completed in about 3.5 seconds and the total number of positions moved during that total time corresponds to 44 all in a clockwise direction around the incubation chamber 12.

During the last frame 216 of the cycle 210, ancillary reagents can be added to appropriate cuvettes and cuvettes are added and exited from the incubation chamber 12. This occurs in a time period of about 3.1 seconds.

Following the 3.1 second time period, the cuvette ring 62 moves in a clockwise direction 8 positions such that the detent pin 168 is aligned under the index mechanism 150. The index mechanism 150 disengages the cuvette ring 62 from the magnet ring 66 as described above in conjunction with FIGS. 6 and 6A and the magnet ring 66 is moved relative the cuvette ring 62. The detent pin 168 then re-engages the cuvette ring 62 to the magnet ring 66. It should be noted that during the index step the cuvette ring 62 is stationary and the magnet ring 66 moves 1 position in a clockwise direction. In alternate embodiments however, it may be desirable to move the cuvette ring 62 rather than the magnet ring 66.

Thus, the total cuvette cycle lasts for a time period of about 15 seconds and in this particular example the cuvette ring 62 has moved a total of 105 positions (53 positions in a counter clockwise direction and 52 positions in a clockwise direction) and has advanced a cuvette around the incubation chamber 12 one cuvette slot. In this embodiment, the cuvette advances toward the magnet in the counter clockwise direction.

It should be noted that during any portion of cuvette cycle 210 a cuvette does not remain in a stationary position for more than 5 seconds even though the total cycle time is 15 seconds. That is, each cuvette is advanced a single position around the incubation chamber 12 and a single position relative to the magnet 130, 144 every 15 seconds. However, no one cuvette remains under a single position of a probe station 24 (FIG. 1) for longer than 5 seconds within the 15 second cuvette cycle time.

Referring now to FIG. 8A, a diagram illustrating the movements of the cuvette and magnet rings 62, 66 during a second different cycle 220 is shown.

The cycle 220 is divided into three frames as was cycle 210 described above in conjunction with FIG. 8. The same operations performed in the first and last frames 212, 216 of cycle 210 can be performed in the first and last frames 212, 216 of cycle 220.

In the cycle 220, however, different operations are performed in frame 222 than those performed in frame 214 of cycle 210. In frame 222 of cycle 220, the cuvette ring moves in a clockwise direction 4 cuvette positions in 0.2 seconds. Then a diluted sample may be dispensed into a clean cuvette. This operation must be completed in about 2.5 seconds. The cuvette ring then moves 40 positions in a clockwise direction in a time period of about 1 second and stops in the ancillary reagent dispense position.

Thus, in cycle 220 the cuvette ring moves a total of 105 positions in about 15 seconds and has advanced a cuvette around the incubation 12 one cuvette slot relative to the magnet pairs 130, 144 disposed on the magnet ring 66.

Referring now to FIG. 8B, a diagram illustrating the movements of the cuvette and magnet rings 62, 66 during a third different system cycle 224 is shown.

As described above in conjunction with FIGS. 8 and 8A, the total cycle 224 is again divided into three time frames 212, 226 and 216. The same operations performed in frames 212, 216 described above in conjunction with FIGS. 8 and 8A can be performed in frames 212, 216 of cycle 224.

In the frame 226, however, the system 10 performs different operations than those performed in the frame 214 of cycles 210 and frame 222 of frame 220. In frame 226 the cuvette ring moves five positions in a counterclockwise direction in about 0.25 seconds. The cuvette ring remains stationary for about 2.5 seconds during which time a diluted sample may be dispensed into a new cuvette at the sample position. Alternatively, or in addition to the above step, a new sample may be disposed into a cuvette.

The cuvette ring then moves 49 positions in a clockwise direction and stops in the ancillary reagent dispense position. Thus, the cuvette ring has moved a total of 115 cuvette ring positions and has advanced a cuvette around the incubation chamber 12 toward the magnet pairs 130, 144 by a distance corresponding to one cuvette slot.

Figure 9:
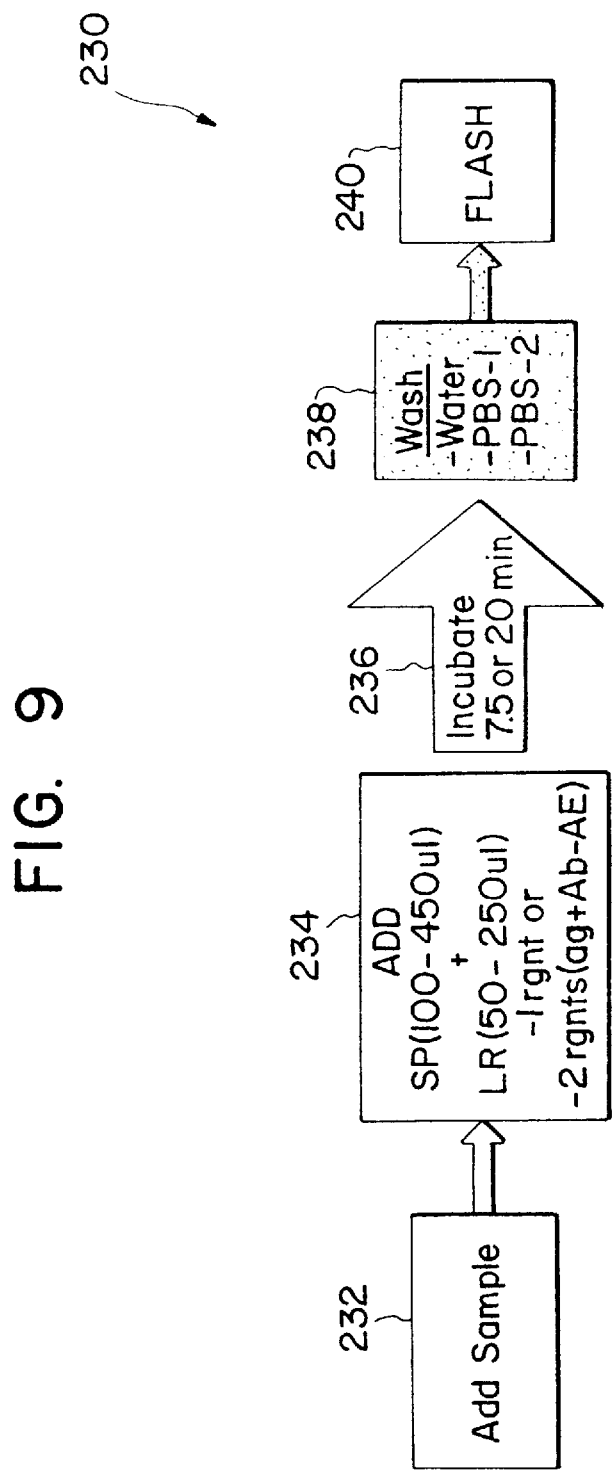
FIGS. 9–9C are a series of flow diagrams illustrating exemplary protocols which may be run in the incubation chamber of the present invention.

Referring now to FIGS. 9–9C, a series of process steps illustrating a plurality of different protocols which can be accommodated in the analyzer system 10 (FIG. 1) are shown. It should be noted that these protocols represent only a small number of a vast plurality of protocols which can be accommodated by the analyzer system 10, and that the protocols here shown are only intended to be representative and illustrative of the types of protocols and protocol steps which can be accommodated in the analyzer system 10 and should not be construed as limiting as to the types of protocols which can be accommodated in the system 10.

Turning now to FIG. 9, a so-called one step protocol is shown. The one step protocol refers to a protocol in which only one wash step is performed.

As shown in FIG. 9 during process step 232 a predetermined amount of a sample is added to a cuvette positioned at the sample probe station in slot 122 of the cuvette ring 62. The precise amount of the sample which is added to the cuvette is selected in accordance with the type of assay being performed but in this particular protocol the sample amount is within the range of about five microliters (ul) to twohundred ul of sample fluid.

Next as shown in process step 234 solid phase and light reagents can be added to the cuvette. Again, the precise amount of either reagent which is added is selected in accordance with the type of assay being performed. In this particular protocol between 100 and 450 ul of a solid phase reagent and between 50–250 ul of a light reagent are added to the cuvette.

Then as shown in process step 236, an incubation period occurs. The incubation period is defined as the period of time between when a first primary reagent is added to the sample fluid in the cuvette and when the cuvette reaches the magnet pair 130 (FIG. 5). In this particular example, the incubation period can last for a time period typically of about eight minutes or alternatively the incubation period can last for a time period typically of about eighteen minutes.

In the event that an eighteen minute incubation time is required, the eighteen minute incubation period is achieved by adding the reagent to the cuvette such that the cuvette remains in the incubation chamber 12 for about eighteen minutes before the cuvette reaches the magnets.

In a test which requires an incubation period of about eighteen minutes, the first reagent should be dispensed into a cuvette which is held in position 92 of the cuvette ring. The reagent, however, is dispensed by a reagent probe which can only access cuvettes in position 29 of the cuvette ring. Thus, the cuvette ring moves the cuvette in position 92 to position 29 for dispensing by the reagent probe.

The first magnet is disposed at position 20 of the cuvette ring which is 72 positions away from position 92. Thus the cuvette and magnets are spaced by a distance of 72 cuvettes positions.

Since each cuvette slot moves relative to the magnet every fifteen seconds (i.e. cuvettes move one cuvette position during one fifteen second cuvette cycle as described in conjunction with FIG. 8 above) the time it takes to index the magnets to position 92 corresponds to about eighteen minutes (72 cuvette positions×15 seconds per cuvette position / 60 seconds per minute=18 minutes). This results in an eighteen minute incubation period. Also another minute or so may pass prior to the first aspirate.

In a test which requires an incubation period of about eight minutes, the reagent is dispensed by probe 241 into a cuvette at position 53 of the cuvette ring 62. The first magnet is location at position 20 on the cuvette ring 62. Thus the cuvette and magnets are spaced by a distance of 33 cuvette positions. Since each cuvette slot moves relative to the magnet every fifteen seconds (i.e. cuvettes move one cuvette position during one fifteen second cuvette cycle as described in conjunction with FIG. 8) the time it takes to index the magnets to position 53 corresponds to about eight minutes (33 cuvette positions×15 seconds per cuvette position / 60 seconds per minute=8.25 minutes). This time is approximate of course since it depends on which part of the cycle at position 53 that the reagents are dispensed and the time when the incubation period actually stops.

There are eleven cuvette positions between reagent probes 241 and 24k and between reagent probes 24k and 24j on the incubation chamber 12. The time it takes a cuvette to travel between these positions is approximately 2.75 minutes (11× 15/60). The ancillary reagent is dispensed from the ancillary reagent probe 24b at position 115. Ancillary reagents are dispensed into cuvettes at position 71 of the cuvette ring. Thus the cuvette ring must move a cuvette at position 71 of the cuvette ring to position 115 of the cuvette ring to allow an ancillary reagent to be dispensed therein. A first reagent is dispensed from reagent probe 241 at position 53 which is 18 cuvette positions away from the ancillary reagent probe. Thus the ancillary incubation time is 4.5 minutes (18×15/60). It should be noted, however, that the ancillary incubation time in an assay having an eighteen minute incubation time will be longer than 4.5 minutes.

After the incubation period is complete then as shown in process step 238 a wash cycle is performed following which the cuvette is passed to the luminometer 14 and as shown in process step 240 a chemiluminescent reaction and resultant light flash is measured via the luminometer 14.

Figure 9A:
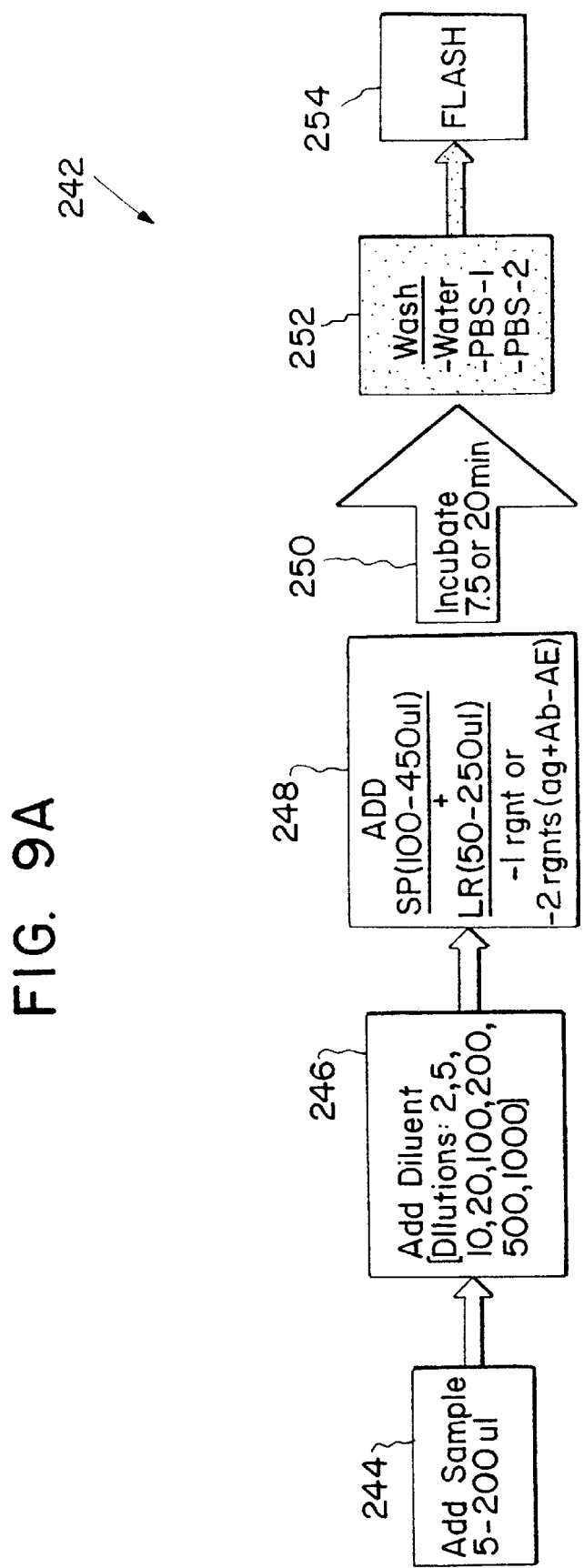

Referring now to FIG. 9A, a so-called one step with dilutions protocol is shown. The one step with dilutions protocol refers to a protocol in which a diluent is added to a cuvette and only one wash step is performed. Sometimes referred to as "Forward Sandwich" assays.

As shown in FIG. 9A during process step 258 a predetermined amount of a sample is added to a cuvette positioned at the sample probe station in slot 111 of the cuvette ring 62. The precise amount of the sample which is added to the cuvette is selected in accordance with the type of assay being performed but in this particular protocol the sample amount is within the range of about five microliters (ul) to two-hundred ul of sample fluid.

Next, as shown in step 246 a diluent is added to the sample to thus dilute the sample. The sample may be diluted by one-half for example or by one thousand times or by any other amount depending upon the assay requirements.

Next as shown in process step 248 solid phase and light reagents can be added to the cuvette. Again, the precise amount of either reagent which is added is selected in accordance with the type of assay being performed. In this particular protocol between 100 and 450 ul of a solid phase reagent and between 50–250 ul of a light reagent are added to the cuvette.

Then as shown in process step 250, an incubation period occurs. As described above in conjunction with FIG. 9, the incubation period is defined as the period of time between when a first primary reagent is added to the sample fluid in the cuvette and when the cuvette reaches the magnet pair 130 (FIG. 5). In this example, the incubation period can last for a time period typically of about eight minutes or alternatively the incubation period can last for a time period typically of about eighteen minutes. The particular incubation times can be achieved as described above in conjunction with FIG. 9. The particular incubation period required depends of course on the type of assay being performed.

After the incubation period is complete then as shown in process step 252 a wash cycle is performed following which the cuvette is passed to the luminometer 14 and as shown in process step 254 a chemiluminescent reaction and resultant light flash is measured via the luminometer 14.

Referring now to FIG. 9B, a so-called two step protocol is shown. The two step protocol refers to a protocol in which two wash steps are performed.

During process step 258 a predetermined amount of a sample is added to a cuvette positioned at the sample probe station in slot 111 of the cuvette ring 62. The precise amount of the sample which is added to the cuvette is selected in accordance with the type of assay being performed but in this particular protocol the sample amount is within the range of about five microliters (ul) to two-hundred ul of sample fluid.

Next as shown in process step 260 solid phase reagents can be added to the cuvette. Again, the precise amount of the solid phase reagent which is added is selected in accordance with the type of assay being performed. In this particular protocol between 100 and 450 ul of a solid phase reagent is added to the cuvette.

Then as shown in process step 262, an incubation period occurs. In this protocol the incubation period lasts for a period of time typically of about eighteen minutes.

Next as shown in process step 264, wash and/or re-suspend operations can be performed following which a light reagent is added as shown in step 266. The precise amount of the light reagent which is added is again selected in accordance with the type of assay being performed. In this particular protocol, between 50 and 250 ul of a light reagent is added to the cuvette.

Then as shown in process step 268, a second incubation period occurs. In this protocol the second incubation period lasts for a period of time typically of about eighteen minutes.

After the second incubation period 268 is complete then as shown in process step 270 a wash cycle is performed following which the cuvette is passed to the luminometer 14 and as shown in process step 272 a chemiluminescent reaction and resultant light flash is measured via the luminometer 14.

Referring now to FIG. 9C, a so-called two step with dilutions protocol is shown. The two step with dilutions protocol refers to a protocol in which a diluent is added to a cuvette and two wash steps are performed.

During process step 276 a predetermined amount of a sample is added to a cuvette positioned at the sample probe station in slot 111 of the cuvette ring 62. The precise amount of the sample which is added to the cuvette is selected in accordance with the type of assay being performed but in this particular protocol the sample amount is within the range of about five microliters (ul) to two-hundred ul of sample fluid.

Next, as shown in step 278 a diluent is added to the sample to thus dilute the sample. The sample may be diluted by one-half for example or by one thousand times or by any other amount depending upon the assay requirements.

Next as shown in process step 280 solid phase reagents can be added to the cuvette. Again, the precise amount of the solid phase reagent which is added is selected in accordance with the type of assay being performed. In this particular protocol between 100 and 450 ul of a solid phase reagent is added to the cuvette.

Then as shown in process step 282, a first incubation period occurs. In this protocol the first incubation period lasts for a period of time typically of about eighteen minutes.

Next as shown in process step 284, wash and re-suspend operations are performed following which a light reagent is added to the cuvette as shown in step 286. The precise amount of the light reagent which is added is again selected in accordance with the type of assay being performed. In this particular protocol, between 50 and 250 ul of a light reagent is added to the cuvette.

Then as shown in process step 288, a second incubation period occurs. In this protocol the second incubation period also lasts for a period of time typically of about eighteen minutes.

After the second incubation period 288 is complete then as shown in process step 290 a wash cycle is performed following which the cuvette is passed to the luminometer 14 and as shown in process step 292 a chemiluminescent reaction and resultant light flash is measured via the luminometer 14. It should be noted that cuvettes following this protocol move twice past the wash stations of the incubation chamber 12.

Referring now to FIGS. 10–14A in which like elements are provided having like reference designations, a portion of an incubation chamber 300 includes a magnet ring 302 having a slot formed therein to accept a cuvette 84. A cuvette ring 304 is disposed in a top portion of the slot in the magnet ring 302 and a first surface of the cuvette ring is slidably disposed over a top surface of the magnet ring 302.

Coupled to the magnet ring 302 is an index detent spring 306. The index detent spring 306 engages slot regions 307 of the cuvette ring 304 to thus couple the cuvette ring 304 to the magnet ring 302 and prevent the cuvette ring 304 from moving relative to the magnet ring 302. A slide bar 308 is disposed over a top surface of an incubation chamber housing 310 and acts as an index lock and release mechanism. An incubation chamber cover 311 (not shown in FIG. 10A) is disposed over the slide bar 308 and housing 310.

In operation, the slide bar 308 pushes against the index detent spring 306 such that the detent spring 306 is forced into a cut out region 312 of the incubation chamber housing 310. This de-couples the magnet and cuvette rings 302, 304 and thus allows the cuvette ring 304 to move relative the magnet ring 302.

The contacting surfaces of the cuvette and magnet rings 302, 304 are preferably provided from materials having a low coefficient of friction or alternatively are coated with a low friction material such as teflon, for example, to thus allow the rings 302, 304 to move with respect to each other with relatively little resistance. It should be noted that in this particular embodiment, a friction bearing between the magnet ring and cuvette ring surfaces may be used since the two rings move relatively slowly with respect to each other and thus tend not to heat up to unreasonable levels or wear rapidly.

The incubation chamber 300 further includes a magnet ring bearing 314 coupled to the magnet ring 302. A drive belt 316 is also coupled to the magnet ring 302. The magnet ring bearing 314 and drive belt 316 may operate in a manner similar to the drive belt 35 and magnet ring bearing 68 described above in conjunction with FIGS. 4, 6 and 6A.

Figure 11:
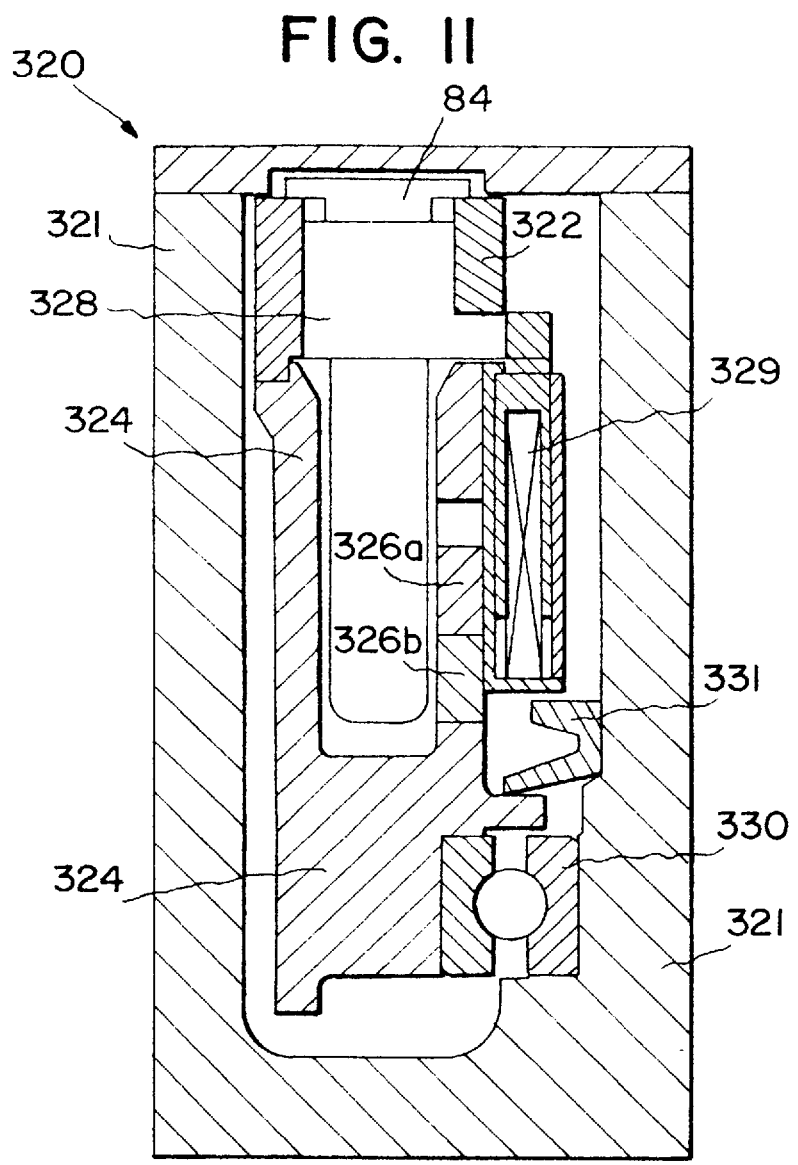
FIG. 11 shows another alternate embodiment of an incubation chamber having separately movable cuvette and magnet rings.

Referring now to FIG. 11, a portion of an incubation chamber 320 includes an incubation chamber housing 321 having disposed therein a cuvette ring 322 movably coupled to a magnet ring 324. The magnet ring 324 is provided having a slot therein into which a cuvette 84 may be disposed. A pair of magnets 326a, 326b are coupled as shown to the magnet ring 324. The cuvette ring 322 is slidably disposed on a first surface of the magnet ring 324. A tooth 328 projecting from a first surface of the cuvette ring 322 separates adjacent cuvettes 84.

The cuvette and magnet rings 322, 324 are preferably provided from materials having a low coefficient of friction or alternatively are coated with a low friction material such as teflon, for example. It should again be noted that in this particular embodiment, a friction bearing between the magnet ring and cuvette ring surfaces may be used since the two rings move relatively slowly with respect to each other and thus tend not to generate excessive heat.

A vertical spring plunger 329 couples the cuvette ring 322 to the magnet ring 324. A plunger similar to the type described above in conjunction with FIGS. 6 and 6A may be used to disengage the vertical spring 329 and thus allow the cuvette ring 322 to move relative the magnet ring 324.

The magnet ring 324 is coupled to a magnet ring bearing 330. In this particular embodiment, a seal 331 is disposed above a magnet ring bearing 330 between a wall of the housing 321 and a wall of the magnet ring 324 to thus prevent fluid which may be inadvertently dispensed outside a cuvette or spill out of a cuvette, for example, from entering the magnet ring bearing 330.

Figure 12:
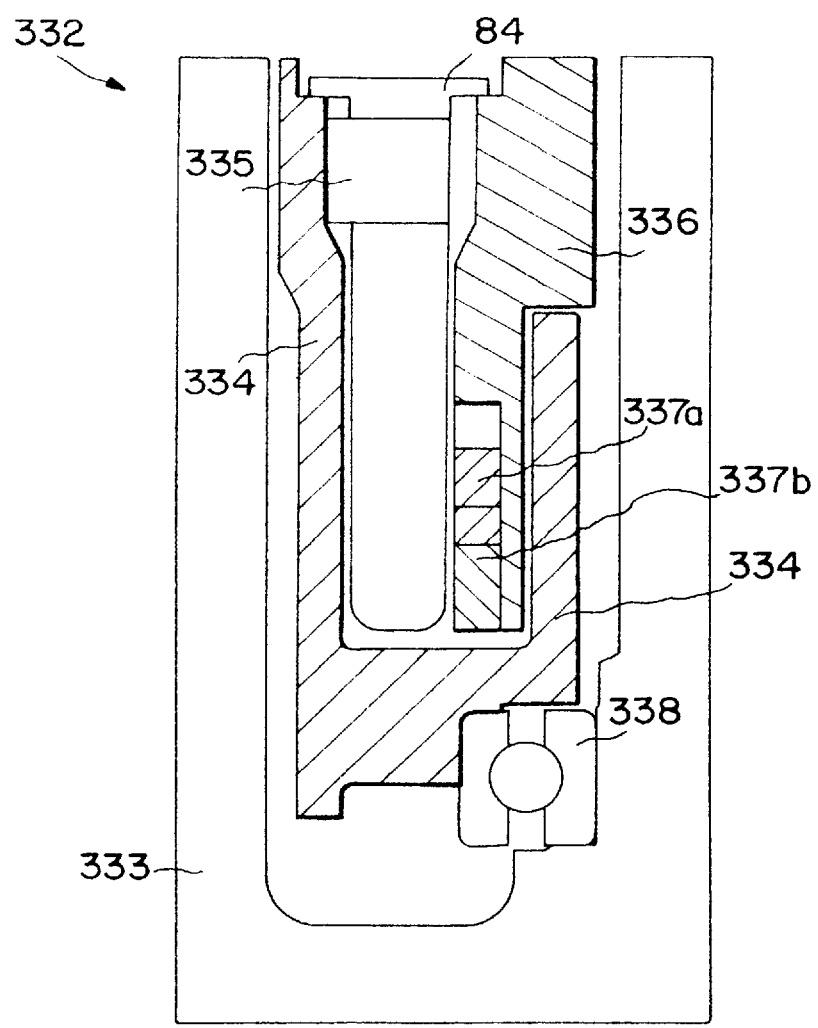
FIG. 12 shows yet another alternate embodiment of an incubation chamber having separately movable cuvette and magnet rings.

Referring now to FIG. 12, a portion of an incubation chamber 332 includes an incubation chamber housing 333 having disposed therein a cuvette ring 334 movably coupled to a magnet ring 336. In this embodiment, walls of the cuvette ring 334 form a slot in which a cuvette 84 and a portion of the magnet ring 336 is disposed. A member 335 projecting from a first surface of the cuvette ring 334 separates adjacent cuvettes 84 disposed in the cuvette ring 334. It should be noted that in this particular embodiment, the cuvette 84 is supported by both the cuvette ring 334 and the magnet ring 336. A pair of magnets 337a, 337b are coupled to the magnet ring 336 adjacent a surface of the cuvette 84.

The cuvette ring 334 is coupled to a cuvette ring bearing 338. The cuvette and magnet rings 334, 336 are provided having a friction fit such that magnet ring 336 and cuvette ring 334 can move relative each other. Thus, the cuvette and magnet rings 334, 336 are provided from materials having a relatively low coefficient of friction or alternatively are coated with a low friction material such as teflon, for example, to thus allow the rings 334, 336 to move with respect to each other with relatively little resistance.

It should again be noted that in this particular embodiment, a friction bearing between the contacting surfaces of the cuvette ring 334 and magnet ring 336 may be used since the two rings move relatively slowly with respect to each other and thus tend not to heat up to unreasonable levels.

Figure 13:
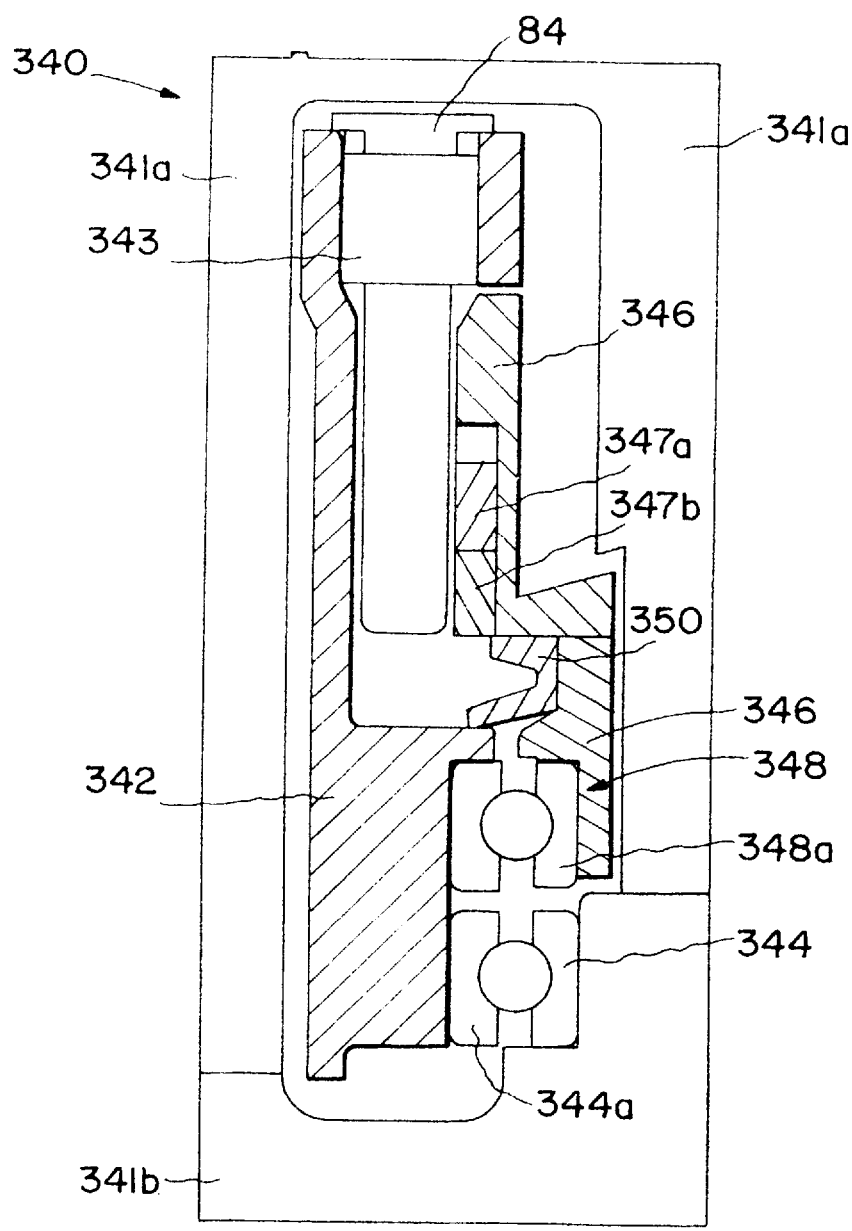
FIG. 13 shows yet another alternate embodiment of an incubation chamber having separately movable cuvette and magnet rings.

Referring now to FIG. 13, a portion of an incubation chamber 340 is shown to include an incubation chamber housing 341 having an upper housing portion 341a and a lower housing portion 341b. In this particular embodiment, a top portion of a cuvette ring 342 has a member 343 which forms a slot into which a cuvette 84 is disposed. A lower portion of the cuvette ring 342 is coupled to an outer race 344a of a cuvette ring bearing 344.

The incubation chamber 340 also includes a magnet ring 346 having a pair of magnets 347a, 347b coupled thereto as shown. One end of the magnet ring 346 is coupled to an inner race 348a of a magnet ring bearing 348. A seal 350 is disposed above the magnet ring bearing 348 and cuvette ring bearing 344 to prevent fluid from entering either of the bearings 344, 348.

By coupling the cuvette and magnet rings 342, 346 to separate bearing assemblies 344, 348 respectively, each of the rings 342, 346 can be driven by a separate motor coupled thereto by separate. belts, for example. Alternatively, the cuvette ring 342 and magnet ring 346 may be coupled together using for example, means similar to the means described above in conjunction with FIGS. 6, 10, 11 and 12.

It should be noted, however, that by providing a separate cuvette ring bearing and magnet ring bearing 344, 348 the magnet ring 346 need not be provided as a complete ring. Rather, the magnet ring 346 could be provided as a quarter or half ring or any other size ring which would allow proper paramagnetic particle separation to occur in a system employing separate magnet and cuvette ring bearings.

Having described preferred embodiments of the invention, it will now become apparent to one of skill in the art that other embodiments incorporating the concepts may be used. It is felt, therefore, that these embodiments should not be limited to disclosed embodiments but rather should be limited only by the spirit and scope of the appended claims.

What is claimed is:

1. An incubation assembly for handling biological samples and test reagents in an automated biological testing system, said assembly comprising:

at least first and second ring segments selectively associated for both fixed and independent rotation in response to control signals, at least one of which ring segments is adapted for holding sample cuvettes in spaced cuvette receiving positions, and at least one other of said ring segments including a sample and reagent condition effector coupled thereto that is selectively applied to a biological sample and a test reagent present in one of said cuvettes by relative rotation of the first and second ring segments in response to said control signals, the sample and reagent condition effector including a magnet comprising at least two magnet segments separated by a split, the magnet operative to attract paramagnetic particles in the sample cuvettes when the second ring is so placed as to have the magnet adjacent selected cuvettes;

at least one sample dosing assembly responsive to said control signals and having a fluid transfer probe for applying a dose of the biological sample to be tested from a sample supply to said one of said cuvettes in one said ring segment at at least one first position to which cuvettes in that ring segment can be rotated;

at least one reagent dosing assembly responsive to said control signals and having a fluid transfer probe for applying a dose of a reagent to be used in testing from a reagent supply to said one of said cuvettes containing the biological sample in one said ring segment at at least one second position to which cuvettes in that ring segment can be rotated;

a cuvette placement assembly having a supply of cuvettes and a cuvette delivery mechanism operative to deliver cuvettes to at least one third position to which a cuvette receiving position in said cuvette holding ring segment can be placed by rotation of said cuvette holding ring segment in response to said control signals;

a cuvette extraction assembly operative to extract sample and reagent containing cuvettes from at least one fourth position to which a cuvette in said at least one cuvette holding ring segment can be placed by rotation of said ring segment in response to said control signals;

at least one wash assembly having one or more probes for withdrawing and supplying fluid at cuvettes in said first ring segment when positioned adjacent one of said magnet segments in response to said control signals to effect removal of undesired artifacts in the cuvettes before extraction;

a resuspend and dispense assembly positioned adjacent the split between the two magnet segments to supply fluid at cuvettes in said first ring segment when positioned adjacent the split between the magnet segments to effect resuspension of particles in the cuvette; and a scheduler of said control signals operative to provide coordinated rotation of said at least first and second ring segments, sample and reagent dosing assemblies and cuvette placement and extraction assemblies for incubation of a sample and reagent in each cuvette for selectable incubation times and activation of the cuvette sample and reagent effector in said at least one second ring segment prior to extraction by said cuvette extraction assembly, the scheduler including, scheduling to selectively locate the sample and reagent condition effector adjacent to a cuvette after a predetermined incubation time variable over a range of sample and test reagent combinations to place the magnet adjacent to a cuvette after a predetermined incubation time variable over a range of sample and reagent combinations, and to coordinate the wash assembly and relative rotation of the first and second rings to provide paramagnetic particle segregation on a cuvette said, removal of the remainder of residual cuvette fluid, injection of a neutral fluid medium, and resuspension of the paramagnetic particles.

2. The incubation assembly of claim 1 wherein said first and second ring segments extend together forming first and second complete rings.

3. The incubation assembly of claim 1 wherein said scheduler provides coordinated placement of said first and second rings and control of said wash assembly for repetition of the fluid removal, injection and resuspension.

4. The incubation assembly of claim 1 wherein said scheduler provides for rotation of said first and second rings in both clockwise and counterclockwise directions.

5. The incubation assembly of claim 2 further including a ring indexing station at which said ring segment having a sample and reagent condition effector is moved one cuvette receiving position relative said ring segment adapted to holding sample cuvettes in response to rotation of a selected one of said first and second ring segments to the indexing station and engagement of an indexing positioner holding said ring segments at selectable relative positions.

6. The incubation assembly of claim 1 wherein said scheduler rotates the one selected ring to an indexing station on a periodic schedule.

7. The incubation assembly of claim 1 wherein said extraction assembly extracts cuvettes to a luminometer having a doser and photosensor to create and detect luminescence in the cuvette representative of properties of each sample under test.

8. The incubation assembly of claim 7 wherein said luminometer includes a cuvette contents remover and cuvette ejector for removing separately cuvette contents and cuvette to waste sites after detection of luminescence in each cuvette.

9. The incubation chamber of claim 1 wherein said scheduler includes data indicating:

a plurality of test protocols for testing sample types with selected reagents for selected sample properties.

10. The incubation assembly of claim 9 wherein the scheduler data further includes an identifier of each sample awaiting test and the associated test protocol to be run for each sample awaiting test.

11. The incubation assembly of claim 10 wherein said scheduler further includes instructions for selecting each sample and placing it in an empty cuvette in said ring segment adapted for holding sample cuvettes where said sample can be tested according to its associated protocol.

12. The incubation of claim 11 wherein said scheduler selects the sample on predetermined prioritization basis.

13. The incubation assembly of claim 12 wherein said predetermined prioritization basis is selected from the group consisting of FIFO and a number of tests per unit time maximization.

14. The incubation assembly of claim 2 further including a bearing structure supporting said first and second ring for relative rotation.

15. The incubation assembly of claim 14 further including an indexing mechanism that positions the first and second rings relative to each other at any one of a plurality of positions corresponding to a number of cuvette receiving positions.

16. The incubation assembly of claim 15 further including an escapement associated with the indexing mechanism that indexes the relative position of the first and second rings by at least the distance between adjacent cuvette receiving positions in response to a trigger.

17. The incubation assembly of claim 16 wherein said trigger is a mechanical arm positioned to engage said escapement upon rotation of said escapement with the first and second rings past said arm.

18. An automated immunoassay analyzer system for handling biological samples and test reagents comprising:

a magnet-supporting ring and a cuvette-supporting ring selectively associated for both fixed and independent rotation in response to control signals, the cuvette-supporting ring being adapted for holding cuvettes in spaced cuvette-receiving positions, the magnet-supporting ring including a magnet assembly coupled thereto that is selectively applicable to a biological sample and a test reagent present in one of the cuvettes by relative rotation of the first and second rings in response to the control signals;

at least one sample dosing assembly responsive to the control signals and having a fluid transfer probe for applying a dose of the biological sample to be tested from a sample supply to one of the cuvettes in the cuvette-supporting ring at at least one first position to which cuvettes in the cuvette-supporting ring are rotatable;

at least one reagent dosing assembly responsive to the control signals and having a fluid transfer probe for applying a dose of a reagent to be used in testing from a reagent supply to the one of the cuvettes containing the biological sample in the cuvette-supporting ring at at least one second position to which cuvettes in the cuvette-supporting ring are rotatable; and a scheduler of the control signals operative to provide coordinated rotation of the magnet-supporting ring and the cuvette-supporting ring fixed together and rotation of one of the magnet-supporting ring and the cuvette-supporting ring independently and activation of the sample and reagent dosing assemblies for incubation of a sample and reagent in each cuvette for selectable incubation times and activation of the magnet assembly in the magnet-supporting ring to effect a particle separation in the one of the cuvettes in the cuvette-supporting ring, the scheduler including scheduling to selectively locate the magnet assembly adjacent to the one of the cuvettes after a predetermined incubation time variable over a range of sample and test reagent combinations by rotation of one of the magnet-supporting ring and the cuvette-supporting ring variably and independently.

19. The system of claim 18 wherein said magnet ring comprises a first magnet coupled to a first surface of said magnet ring.

20. The system of claim 19 wherein said magnet ring further comprises a second magnet coupled to the first surface of said magnet ring and spaced a predetermined distance from said first magnet.

* * * * *